United States Patent
Sakuma et al.

(10) Patent No.: US 7,119,104 B2
(45) Date of Patent: Oct. 10, 2006

(54) ACTIVATOR OF PEROXISOME PROLIFERATOR-ACTIVATED RECEPTOR DELTA

(75) Inventors: Shogo Sakuma, Saitama (JP); Tomio Yamakawa, Chiba (JP); Takashi Kanda, Chiba (JP); Seiichiro Masui, Saitama (JP)

(73) Assignee: Nippon Chemiphar, Co., Ltd., Tokyo (JP)

( * ) Notice: Subject to any disclaimer, the term of this patent is extended or adjusted under 35 U.S.C. 154(b) by 0 days.

(21) Appl. No.: 10/491,935

(22) PCT Filed: Oct. 9, 2002

(86) PCT No.: PCT/JP02/10472

§ 371 (c)(1),
(2), (4) Date: Oct. 29, 2004

(87) PCT Pub. No.: WO03/033493

PCT Pub. Date: Apr. 24, 2003

(65) Prior Publication Data

US 2005/0096363 A1 May 5, 2005

(30) Foreign Application Priority Data

Oct. 12, 2001 (JP) .............................. 2001-315694

(51) Int. Cl.
- C07D 413/06 (2006.01)
- C07D 413/14 (2006.01)
- C07D 417/06 (2006.01)
- A61K 31/4178 (2006.01)
- A61K 31/423 (2006.01)
- A61K 31/427 (2006.01)

(52) U.S. Cl. ...................... 514/311; 514/338; 514/365; 514/373; 514/374; 514/397; 546/167; 546/270.4; 546/271.4; 546/272.1; 546/272.7; 548/181; 548/206; 548/236; 548/241; 548/311.4

(58) Field of Classification Search ................ 546/167, 546/270.4, 271.4, 272.1, 272.7; 548/181, 548/206, 236, 241, 311.4; 514/365, 373, 514/374, 379, 397

See application file for complete search history.

(56) References Cited

U.S. PATENT DOCUMENTS

| | | | |
|---|---|---|---|
| 5,089,514 A | 2/1992 | Hulin | 514/374 |
| 5,723,479 A | 3/1998 | Sohda et al. | 514/369 |
| 6,043,264 A | 3/2000 | Ohtake et al. | 514/374 |
| 6,300,364 B1 | 10/2001 | Shimokawa et al. | 514/415 |
| 6,589,969 B1 | 7/2003 | Tajima et al. | 514/374 |
| 6,867,224 B1* | 3/2005 | Cheng et al. | 514/365 |
| 2002/0032330 A1 | 3/2002 | Nomura et al. | 546/23 |
| 2005/0054674 A1* | 3/2005 | Sakuma et al. | 514/314 |

FOREIGN PATENT DOCUMENTS

| | | |
|---|---|---|
| EP | 505322 | 9/1992 |
| WO | WO 92/10468 | 6/1992 |
| WO | WO 96/20935 | 7/1996 |
| WO | WO 96/35688 | 11/1996 |
| WO | WO 97/27190 | 7/1997 |
| WO | WO 97/28115 | 8/1997 |
| WO | WO 01/79197 | 10/2001 |

OTHER PUBLICATIONS

He, T.-C. et al., 1999, *Cell* 99:335-345.
Isseman, I. et al., 1990, *Nature* 347:645-650.
Kliewer, S. et al., 1992, *Nature* 358:771-774.
Kliewer, S. et al., 1994, *Proc Natl Acad Sci USA* 91:7335-7359.
Lehmann, J. et al., 1997, *J Biol Chem* 272(6):3406-3410.
Mano H., et al., 2000, *J Biol Chem* 175:8126-8132.

* cited by examiner

Primary Examiner—Fiona T. Powers
(74) Attorney, Agent, or Firm—Jones Day

(57) ABSTRACT

A compound represented by the formula (I) or a salt of the compound, and a PPAR-δ activator which contains the compound or salt as the active ingredient:

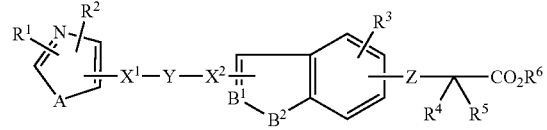

(wherein A represents O or S; $B^1$ represents N, etc.; $B^2$ represents O, etc.; each of $X^1$ and $X^2$ represents O, S, a bond, etc.; Y represents $C_{1-8}$ alkylene chain; Z represents O or S; $R^1$ represents aryl, etc. which can have substituents; $R^2$ represents $C_{1-8}$ alkyl, etc.; $R^3$ represents $C_{1-8}$ alkyl, $C_{2-8}$ alkenyl, etc.; each of $R^4$ and $R^5$ represents hydrogen, $C_{1-8}$ alkyl, etc.; and $R^6$ represents hydrogen, etc.; provided that each of Z and $R^3$ is attached to the benzene ring, and $X^2$ is not attached to the benzene ring).

10 Claims, No Drawings

ACTIVATOR OF PEROXISOME PROLIFERATOR-ACTIVATED RECEPTOR DELTA

TECHNICAL FIELD

The present invention relates to an activator of peroxisome proliferator activated receptor δ.

PRIOR ART

The peroxisome is a small organ present in cells of animals and plants, and its matrix contains various enzymes such as catalases. Various compounds such as fibrates, herbicides, and phthalic acid plasticizers are known as peroxisome proliferators which induce proliferation of peroxisomes.

Isseman, et al. have identified a nuclear receptor which is activated by peroxisome proliferator and called it peroxisome proliferator activated receptor (PPAR).—Nature, 347, p645–650, 1990.

Three subtypes such as PPARα, PPARγ and PPARδ have been identified.—Proc. Natl. Acad. Sci. USA, 91, p7335–7359, 1994.

The above-mentioned fibrates used as the serum triglyceride (TG) lowering drug can modulates PPARδ activity.

Further, thiazolidine compounds (Troglitazone, Rosiglitazone, Pioglitazone) useful in the treatment of diabetes are also known as ligands of PPARγ.

It is reported that several compounds such as GW-2433 (Glaxo Wellcome), L-165041 (Merck), and YM-16638 (Yamanouchi Pharmaceutical) activate PPARδ. Each formula is as follows:

WO 92/10468 describes that GW-2433 can be used for prevention and treatment of atherosclerosis.

WO 97/28115 describes that L-165041 can be used for treatment of diabetes and suppression of obesity.

WO 99/04815 describes that YM-16638 shows effects for reducing serum cholesterol and reducing LDL cholesterol.

Recently, JBC, 272(6), p3406–3410, 1997 and Cell, 99, p335–345, 1999 describe proposal for application of PPAR δ ligand as an anti-cancer agent and an anti-inflammatory agent.

The following compounds A to E have a structure similar to the compound of the present invention (mentioned below), in more detail a benzisoxazole derivative of the general formula (I). The compound A is disclosed in Japanese Patent No. 2,581,523, the compound B is disclosed in WO 98/28254, the compound C is disclosed in Japanese Patent Provisional Publication No. 8(1996)-311065, the compound D is disclosed in WO 97/27190, and the compound E is disclosed in WO 96/20935. Each formula is as follows:

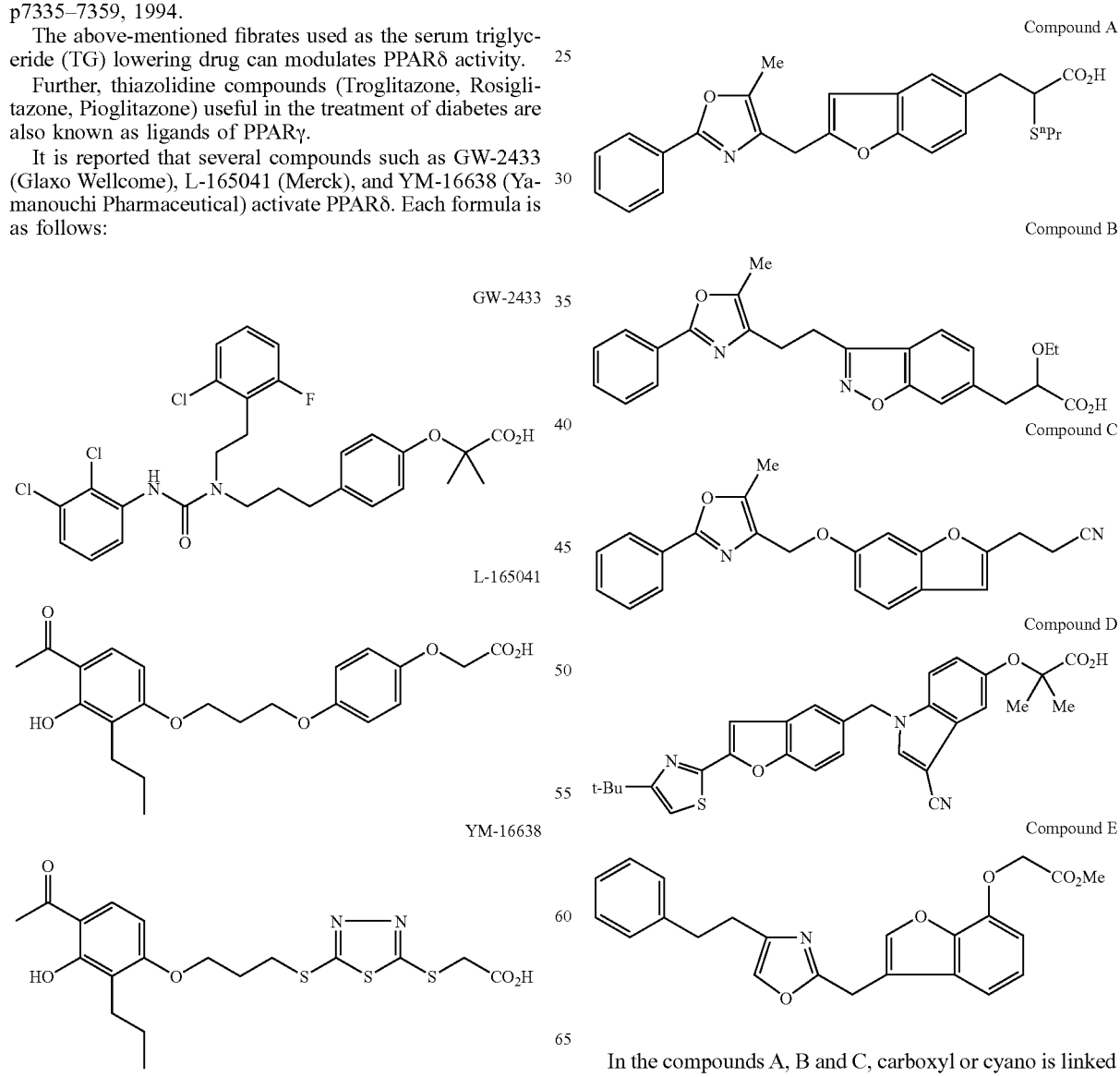

In the compounds A, B and C, carboxyl or cyano is linked by an alkylene chain (which can be substituted with ethoxy or propylthio at the α-position) to the right side of the benzisoxazole or benzofuran ring.

The compound of the invention has a structure different from the compounds A, B and C. In the compound of the invention, acetic acid or a 2-alkylpropionic acid is linked by an ether or thioether bond to the 5th to 7th position of the benzisoxazole ring.

It has been reported that the compounds A, B and C have an effect of improving insulin resistance or decreasing blood glucose. However, no mention is given with respect to an effect as PPARδ ligand.

In the compound D, benzofuran ring is linked by an alkylene chain to the 1st position of the indole ring.

The compound of the invention has a structure different from the compound D. In the compound of the invention, the thiazole or oxazole ring is linked by an alkylene chain to the 3rd position of the benzisoxazole ring. WO 97/27190 describes that the ACAT (acyl coenzyme A—cholesterol acyltransferase). However, no mention is given with respect to an effect as PPARδ ligand.

In the compound E, the oxazole ring is substituted with only phenethyl at 4th position, and the benzene ring moiety of the benzofuran ring has only methoxycarbonyl-methoxy. The compound of the invention has a structure different from the compound E. In the compound of the invention, the oxazole (or thiazole) ring has two substituent groups such as a substituted phenyl and isopropyl, and the benzene ring moiety of the benzofuran ring (benzisoxazole ring) has a substituent group such as propyl, propenyl in addition to alkoxy substituted with carboxyl. WO 96/20935 describes that the compound E has an antagonistic effect against $TXA_2$ receptor. However, no mention is given with respect to an effect as PPARδ ligand.

The present inventors have been filed WO 01/79197, which relates to benzisoxazole derivatives. In the compounds of the Examples in the patent application, the benzisoxazole ring has no substituent. On the other hand, the compound of the present invention has benzisoxazole ring having at least one substituent.

An object of the present invention is to provide a compound having the following general formula (I), which has an effect of activating peroxisome proliferator activated receptor δ.

[Disclosure of Invention]

The invention resides in a compound having the following general formula (I) or a salt thereof:

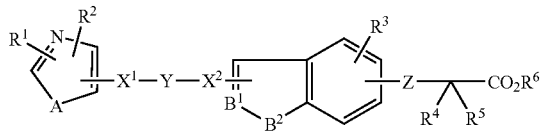

(wherein A is O, S or $NR^7$ in which $R^7$ is hydrogen or $C_{1-8}$ alkyl;

$B^1$ is CW or N in which W is hydrogen or a bond;

$B^2$ is O, S or $NR^8$ in which $R^8$ is hydrogen or $C_{1-8}$ alkyl;

each of $X^1$ and $X^2$ is O, S, NH, NHC(=O)., C(=O), C(=N—$OR^9$), CH($OR^{10}$), C=C, C≡C or a bond in which each of $R^9$ and $R^{10}$ is hydrogen or $C_{1-8}$ alkyl;

Y is a $C_{1-8}$ alkylene chain, which can be substituted with $C_{1-8}$ alkyl or $C_{1-8}$ alkyl substituted with 1–3 halogens;

Z is NH, O or S $R^1$ is aryl, which can be substituted with a group or atom selected from the group consisting of $C_{1-8}$ alkyl, $C_{1-8}$ alkoxy, $C_{1-8}$ alkyl substituted with 1–3 halogens, hydroxyl, nitro, amino, phenyl, pyridyl and halogen, or a heterocyclic group having five to eight membered ring comprising one to three hetero atoms selected from the group consisting of nitrogen, oxygen and sulfur and the other atoms consisting of carbon (benzene ring can be condensed with the heterocyclic ring);

$R^2$ is $C_{2-8}$ alkyl, $C_{1-8}$ alkyl substituted with 1–3 halogens, $C_{3-7}$ cycloalkyl, $C_{2-8}$ alkenyl, $C_{2-8}$ alkynyl, alkyl (comprising $C_{1-4}$ alkyl moiety) substituted with aryl, which can be substituted with a group or atom selected from the group consisting of $C_{1-8}$ alkyl, $C_{1-8}$ alkoxy, $C_{1-8}$ alkyl substituted with 1–3 halogens, hydroxyl, nitro, amino, phenyl, pyridyl and halogen, or alkyl (comprising $C_{1-4}$ alkyl moiety) substituted with a heterocyclic group having five to eight membered ring (comprising one to three hetero atoms selected from the group consisting of nitrogen, oxygen and sulfur and the other atoms consisting of carbon);

$R^3$ is halogen, trifluoromethyl, $C_{1-8}$ alkyl, $C_{2-8}$ alkenyl or $C_{2-8}$ alkynyl;

each of $R^4$ and $R^5$ is hydrogen, $C_{1-8}$ alkyl or $C_{1-8}$ alkyl substituted with 1–3 halogens; and $R^6$ is hydrogen, $C_{1-8}$ alkyl substituted with amino, $C_{1-8}$ alkyl or alkali metal;

provided that each of Z and $R^3$ is attached to the benzene ring, and $X^2$ is not attached to the benzene ring.

The invention also provides an activator of peroxisome proliferator activated receptor δ, which contains as an effective component a compound of the formula (I) or a salt thereof.

DETAILED DESCRIPTION OF THE INVENTION

In the formula (I), $R^3$, $R^4$, $R^5$, $R^6$, $R^7$, $R^8$, $R^9$, $R^{10}$, the substituent of the alkylene chain of Y, the substituent of the aryl and the heterocyclic group of $R^3$, the substituent of the alkyl group substituted with aryl of $R^2$, and the substituent of the alkyl group substituted with a heterocyclic group of $R^2$ can be an alkyl group having 1–8 carbon atoms. Examples of the alkyl groups include methyl, ethyl, propyl, isopropyl, butyl, isobutyl, t-butyl, pentyl and hexyl.

$R^2$ can be an alkyl group having 2–8 carbon atoms. Examples of the alkyl groups include ethyl, propyl, isopropyl, butyl, isobutyl, t-butyl, pentyl and hexyl.

$R^2$, $R^4$, $R^5$, the substituent of the alkylene chain of Y, the substituent of the aryl or heterocyclic group of $R^1$, the substituent of the alkyl group substituted with aryl of $R^2$, and the substituent of the alkyl group substituted with a heterocyclic group of $R^2$ can be an alkyl groups having 1–8 carbon atoms substituted with 1–3 halogens. Examples of the haloalkyl groups include methyl, ethyl, propyl, isopropyl, butyl, and t-butyl which are substituted with 1–3 halogens such as fluorine, chlorine, and bromine. Trifluoromethyl, chloromethyl, 2-chloroethyl, 2-bromoethyl and 2-fluoroethyl are preferred.

$R^2$ and $R^3$ can be an alkenyl group having 2–8 carbon atoms. Examples of the alkenyl groups include vinyl and allyl.

$R^2$ and $R^3$ can be an alkynyl group having 2–8 carbon atoms. Examples of the alkynyl groups include propargyl.

$R^3$ can be a halogen atom. Examples of the halogen atoms include fluorine, chlorine and bromine.

$R^2$ can be a cycloalkyl group having 3–7 carbon atoms. Examples of the cycloalkyl groups include cyclopropyl, cyclopentyl and cyclohexyl.

The substituent of the aryl or heterocyclic group of $R^1$, the substituent of the alkyl group substituted with aryl of $R^2$, and the substituent of the alkyl group substituted with a heterocyclic group of $R^2$ can be an alkoxy groups having 1–8 carbon atoms. Examples of the alkoxy groups include methoxy, ethoxy, propoxy, isopropoxy, butoxy, isobutoxy, t-butoxy, pentyloxy and hexyloxy.

$R^1$ and the aryl moiety of the aryl substituted with alkyl of $R^2$ can be an aryl group. Examples of the aryl groups include phenyl and naphthyl.

$R^1$ and the substituent of the alkyl group of $R^2$ can be a heterocyclic group having five to eight membered ring. Examples of the heterocyclic groups include pyridyl, thienyl, furyl, thiazolyl and quinolyl.

$R^1$ can be a heterocyclic group having five to eight membered ring comprising one to three hetero atoms selected from the group consisting of nitrogen, oxygen and sulfur and the other atoms consisting of carbon. A benzene ring can be condensed with the heterocyclic ring. Examples of the condensed rings include quinoline ring and benzothiophene ring.

Y can be an alkylene chain having 1 to 8 carbon atoms. Examples of the alkylene chains include methylene and ethylene.

$R^3$ can be one to three groups. Two or three groups of $R^3$ can be different from each other.

$R^6$ can be an alkyl group having 1–8 carbon atoms substituted with amino. Examples of the aminoalkyl groups include methyl, ethyl, propyl, isopropyl, butyl, isobutyl, t-butyl, pentyl and hexyl which are substituted with an amino group such as piperidino, pyrrolidino, dimethylamino, and diethylamino.

(1) A preferred compound of the invention is a compound of the formula (I) or salt thereof, in which $R^1$ is attached to the 2nd position of the oxazole, thiazole or imidazole ring.

(2) Another preferred compound of the invention is a compound of the formula (I), a salt thereof or (1), in which $B^1$ is N, and $B^2$ is O.

(3) A further preferred compound of the invention is a compound of the formula (I), a salt thereof, (1) or (2), in which $R^6$ is hydrogen.

(4) A furthermore preferred compound of the invention is a compound of the formula (I), a salt thereof, (1), (2) or (3), in which $X^2$ is a bond.

(5) A still further preferred compound of the invention is a compound of the formula (I), a salt thereof, (1), (2), (3) or (4), in which $X^1$ is a bond.

(6) A still further preferred compound of the invention is a compound of the formula (I), a salt thereof, (1), (2), (3), (4) or (5), in which $R^1$ is aryl substituted with a group or atom selected from the group consisting of $C_{1-8}$ alkyl, $C_{1-8}$ alkoxy, $C_{1-8}$ alkyl substituted with 1–3 halogens, hydroxyl, nitro, amino, phenyl, pyridyl and halogen.

(7) A still further preferred compound of the invention is a compound of the formula (I), a salt thereof, (1), (2), (3), (4), (5) or (6), in which $R^2$ is $C_{2-8}$ alkyl.

(8) A still further preferred compound of the invention is a compound of the formula (I), a salt thereof, (1), (2), (3), (4), (5), (6) or (7), in which $R^3$ is $C_{1-8}$ alkyl or $C_{2-8}$ alkenyl.

The compound of the formula (I) can be in the form of pharmaceutically acceptable salts such as alkali metal salts, e.g., sodium salt and potassium salt.

The processes for preparing the benzisoxazole derivative of the formula (I) are described below.

[Synthetic Process 1]

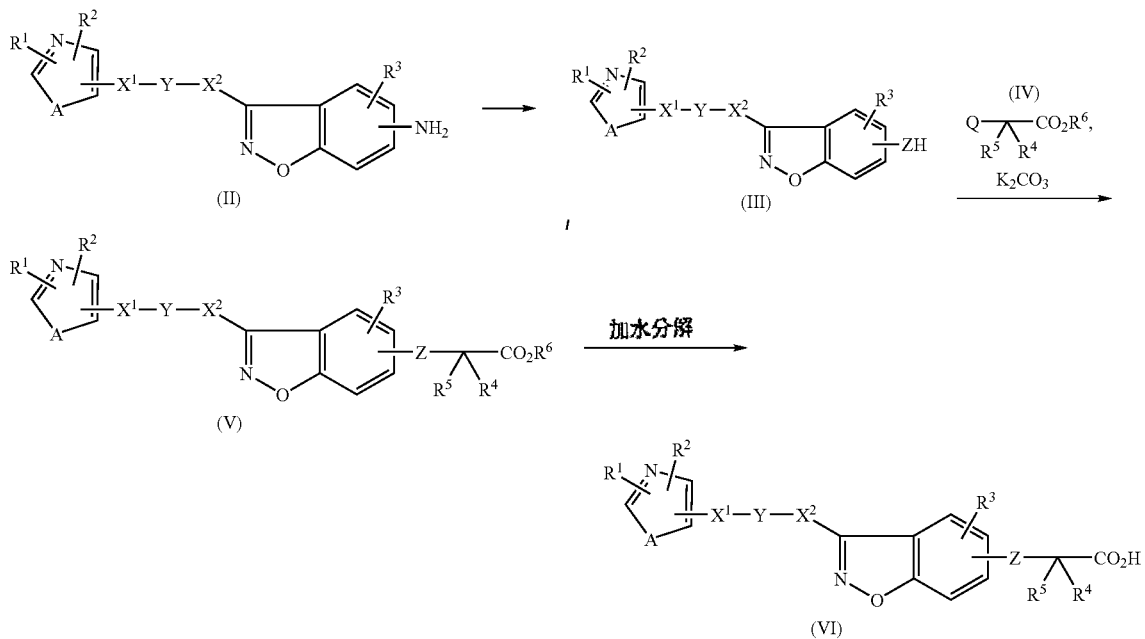

(In the formulas, R is an alkyl group having 1–6 carbon atoms such as methyl, ethyl, Q is a releasing group such as chlorine, bromine, and $R^1$, $R^2$, $R^3$, $R^4$, $R^5$, A, $X^1$, Y, $X^2$ and Z are those described hereinbefore).

The hydroxyl (or mercapto)benzisoxazole derivative of the formula (III) can be prepared by diazotizing the aminobenzisoxazole derivative of the formula (II) with sodium nitrite and a mineral acid (sulfuric acid) while cooling with ice, and decomposing the product with sulfuric acid where Z is oxygen, or reacting the product with potassium ethylxanthate and heating it where Z is sulfur.

The benzisoxazole derivative of the formula (V) according to the invention can be prepared by reacting the compound of the formula (III) with the acetic ester derivative of the formula (IV) in the presence of a base such as potassium carbonate.

The benzisoxazole derivative of the formula (VI) according to the invention can be prepared by subjecting the benzisoxazole derivative of the formula (V) according to the invention to hydrolysis in the presence of lithium hydroxide or potassium hydroxide.

In the case that $R^3$ is allyl, the starting material represented by the formula (III) can be synthesized according to the following reaction scheme.

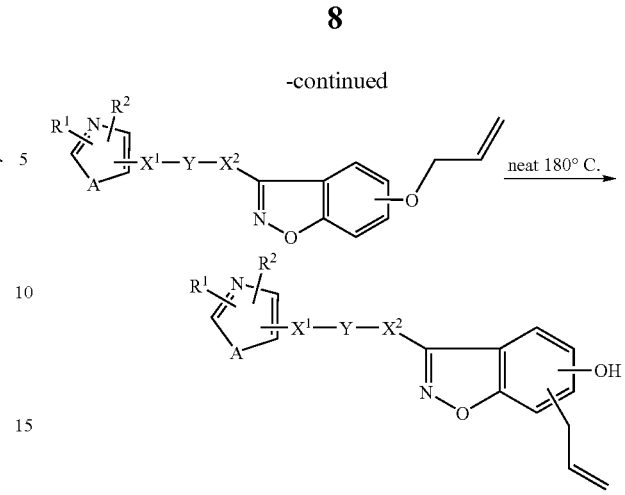

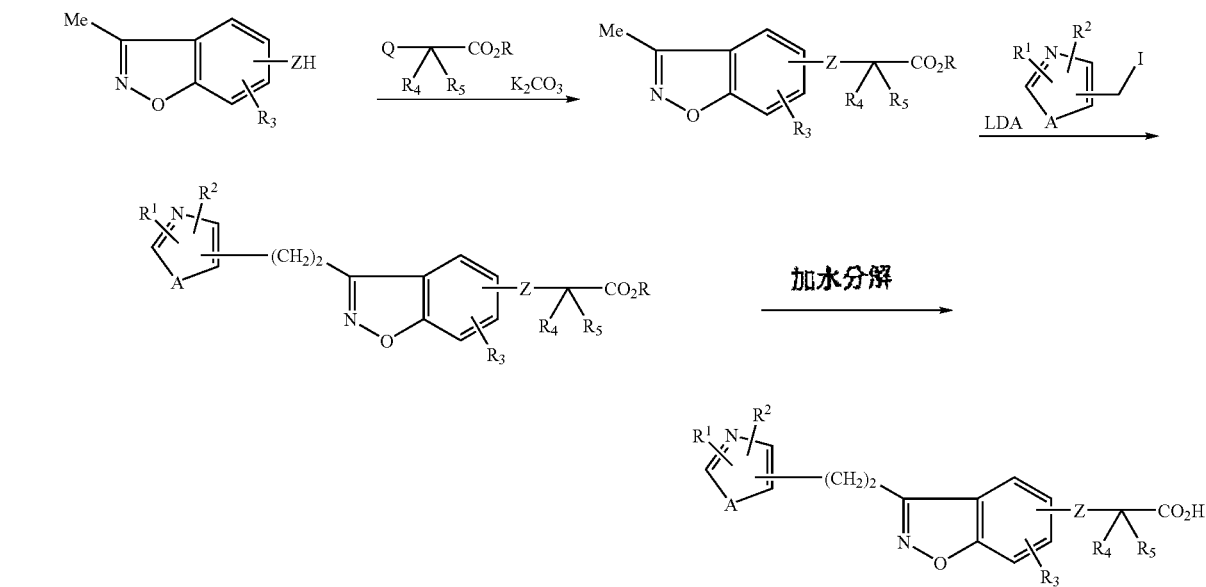

(In the formulas, A, $R^1$, $R^2$, $X^1$, $X^2$ and Y are those described hereinbefore).

[Synthetic Process 2]

The benzisoxazole derivative of the invention can be prepared according to the following reaction scheme.

(In the formulas, A, $R^1$, $R^2$, $R^3$, $R^4$, $R^5$, Z, Q and R are those described hereinbefore).

[Synthetic Process 3]

The benzisoxazole derivative of the invention can also be prepared according to the following reaction scheme.

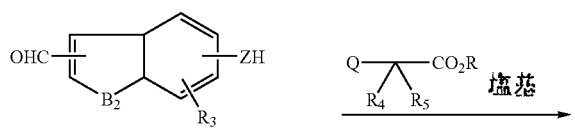

-continued

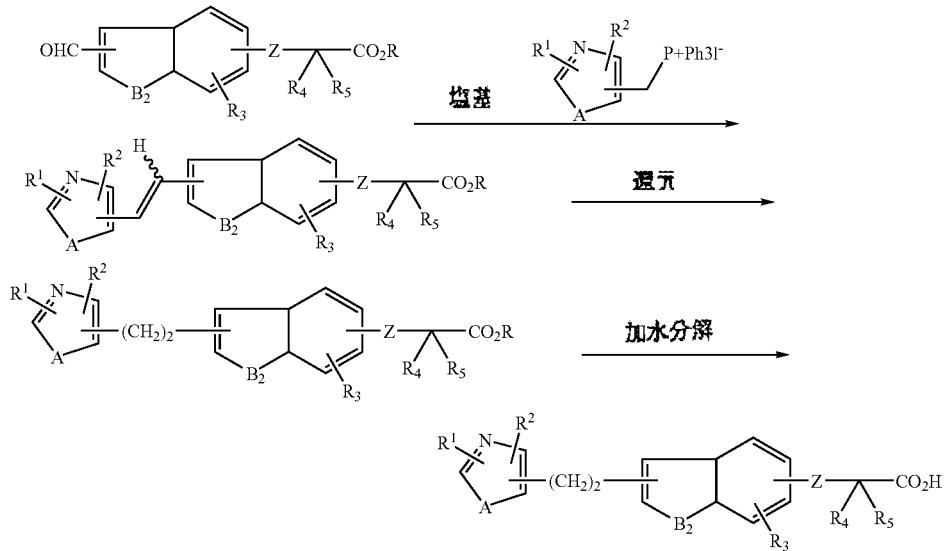

(In the formulas, R, Q, $R^1$, $R^2$, $R^3$, $R^4$, $R^5$, $B^2$, A and Z are those described hereinbefore).

The staring materials of the above-mentioned reaction scheme, namely hydroxyindolealdehyde and hydroxybenzothiophenealdehyde can be prepared, for example by referring the processes disclosed in WO 96/35688, EP 505322.

[Synthetic Process 4]

The compound of the invention wherein $R^3$ is propyl can be prepared according to the following reaction scheme.

(In the formulas, A, $R^1$, $R^2$, $R^4$, $R^5$, $X^1$, $X^2$, Y, Z and R are those described hereinbefore).

The other compounds represented by the formula (I) can also be prepare according to an analogous method.

The prepared compounds according to the invention are set forth in Tables 1 to 24.

(Typical Compounds 1)

The compounds of the invention wherein $X^2$ is a bond, $B^1$ is N, $B^2$ is O, $R^6$ is H are shown in Tables 1 to 5 (in which

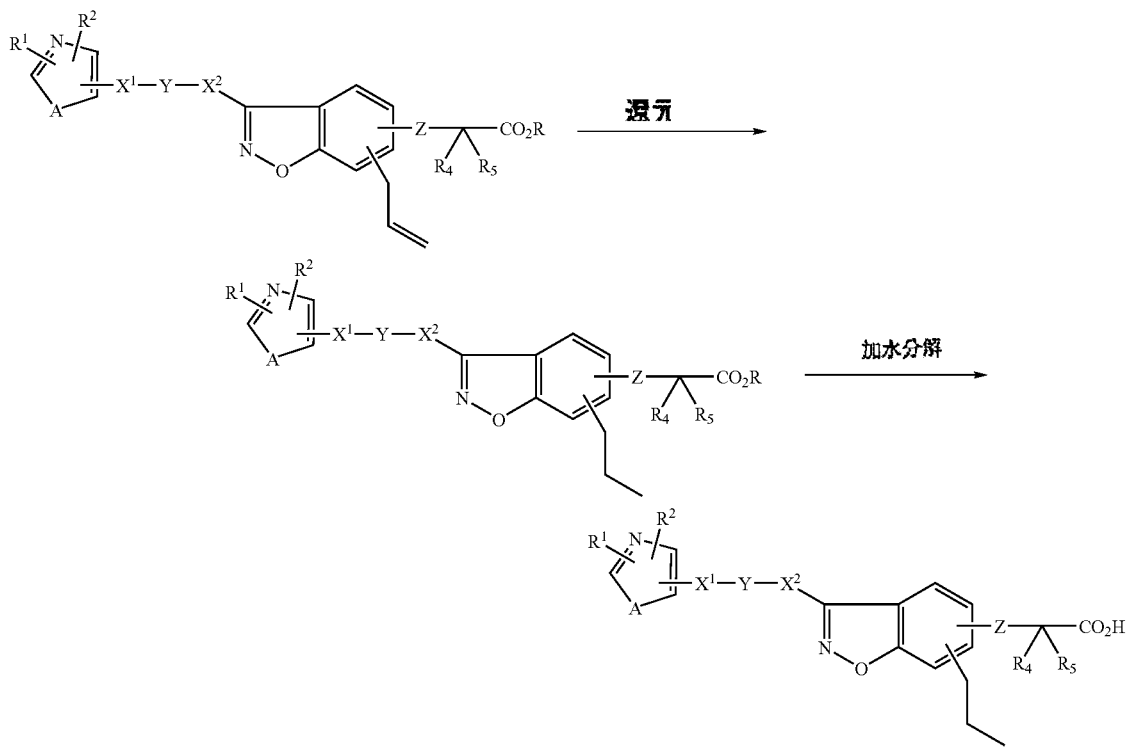

$R^1$ is a substituent at the 2nd position of the imidazole, oxazole or thiazole ring, and $R^2$ is a substituent at the 4th position of the imidazole, oxazole or thiazole ring).

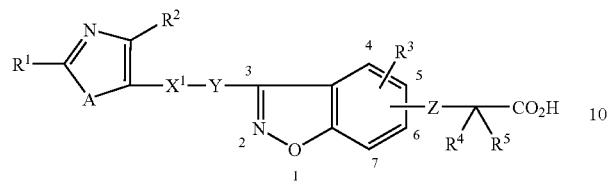

TABLE 1

| $R^1$ | $R^2$ | $R^3$ (position of substitution) | $R^4$ | $R^5$ | A | $X^1$ | Y | Z (position of substitution) |
|---|---|---|---|---|---|---|---|---|
| (4-$CF_3$) Phenyl | Isopropyl | Allyl (7) | Me | Me | S | Bond | $CH_2$—$CH_2$ | O (6) |
| (4-Cl) Phenyl | Isopropyl | Methyl (7) | H | H | S | Bond | $CH_2$—$CH_2$ | O (6) |
| (4-t-Bu) Phenyl | Isopropyl | Methyl (5, 7) | Me | Me | O | Bond | $CH_2$—$CH_2$ | O (6) |
| (3,4-Cl) Phenyl | Isopropyl | Propyl (7) | H | H | S | Bond | $CH_2$—$CH_2$—$CH_2$ | O (6) |
| (3,4-Me) Phenyl | Isopropyl | Butyl (7) | Me | Et | S | Bond | $CH_2$—$CH_2$ | S (6) |
| (2,4-F) Phenyl | Isopropyl | Hexyl (7) | Me | H | S | Bond | $CH_2$—$CH_2$ | O (6) |
| (2,3-F) Phenyl | Isopropyl | Isopropyl (7) | Me | Et | O | NHCO | $CH_2$—$CH_2$ | O (6) |
| (4-OMe) Phenyl | Isopropyl | 2-Propynyl (7)) | H | H | NH | Bond | $CH_2$—$CH_2$ | O (6) |
| 4-Acetyl-phenyl | Isopropyl | 2-Butenyl (7) | H | H | NMe | Bond | $CH_2$—$CH_2$ | O (6) |

TABLE 2

| $R^1$ | $R^2$ | $R^3$ (position of substitution) | $R^4$ | $R^5$ | A | $X^1$ | Y | Z (position of substitution) |
|---|---|---|---|---|---|---|---|---|
| 4-Cyclohexylphenyl | Isopropyl | 2-Pentenyl (7) | Me | Me | S | Bond | $CH_2$—$CH_2$ | S (6) |
| (4-$NO_2$) Phenyl | Isopropyl | Isobutyl (5) | H | H | S | Bond | $CH_2$—$CH_2$ | O (6) |
| (4-$NH_2$) Phenyl | Isopropyl | t-Butyl (5) | Me | Me | O | Bond | $CH_2$—$CH_2$ | O (6) |
| (4-$NMe_2$) Phenyl | Isopropyl | Allyl (5) | H | H | S | CONH | $CH_2$—$CH_2$ | O (6) |
| (3,4,5-Me) Phenyl | Isopropyl | Methyl (5) | Me | Me | S | Bond | $CH_2$—$CH_2$ | O (6) |
| (3,5-Me,4-OH) Phenyl | Isopropyl | Methyl (5, 7) | Me | H | S | Bond | $CH_2$—$CH_2$ | S (6) |
| 3-Pyridyl | Isopropyl | Propyl (7) | Me | Et | O | Bond | $CH_2$—$CH_2$ | O (6) |
| 2-Pyridyl | Isopropyl | Butyl (7) | H | H | NH | CH(OH) | $CH_2$—$CH_2$ | O (6) |
| 3-Pyridyl | Isopropyl | Hexyl (7) | H | H | NMe | Bond | $CH_2$—$CH_2$ | O (6) |

TABLE 3

| $R^1$ | $R^2$ | $R^3$ (position of substitution) | $R^4$ | $R^5$ | A | $X^1$ | Y | Z (position of substitution) |
|---|---|---|---|---|---|---|---|---|
| 2-Naphthyl | Isopropyl | Isopropyl (7) | Me | Me | S | Bond | $CH_2$—$CH_2$ | O (6) |
| 1-Naphthyl | Isopropyl | 2-Propynyl (7) | H | H | S | Bond | $CH_2$—$CH_2$ | S (6) |

TABLE 3-continued

| R$^1$ | R$^2$ | R$^3$ (position of substitution) | R$^4$ | R$^5$ | A | X$^1$ | Y | Z (position of substitution) |
|---|---|---|---|---|---|---|---|---|
| 2-Quinolyl | Isopropyl | 2-Butenyl (7) | Me | Me | O | CO | CH$_2$—CH$_2$ | O (6) |
| (4-CF$_3$) Phenyl | Propyl | 2-Pentenyl (7) | H | H | S | Bond | CH$_2$—CH$_2$ | O (6) |
| (4-Cl) Phenyl | Hexyl | Isobutyl (5) | Me | Me | S | Bond | CH$_2$—CH$_2$—CH$_2$ | O (6) |
| (4-t-Bu) Phenyl | Butyl | t-Butyl (5) | Me | H | S | Bond | CH$_2$—CH$_2$ | O (6) |
| (3,4-Cl) Phenyl | Isobutyl | Allyl (7) | Me | Et | O | Bond | CH$_2$—CH$_2$ | S (6) |
| (3,4-Me) Phenyl | Ethyl | Methyl (7) | H | H | NH | Bond | CH$_2$—CH$_2$ | O (6) |
| (2,4-F) Phenyl | Propyl | Methyl (5, 7) | H | H | NMe | Bond | CH$_2$—CH$_2$—CH$_2$ | O (6) |

TABLE 4

| R$^1$ | R$^2$ | R$^3$ (position of substitution) | R$^4$ | R$^5$ | A | X$^1$ | Y | Z (position of substitution) |
|---|---|---|---|---|---|---|---|---|
| (2,3-F) Phenyl | Hexyl | Propyl (7) | Me | Me | S | Bond | CH$_2$—CH$_2$ | O (6) |
| (4-OMe) Phenyl | Butyl | Butyl (7) | H | H | S | Bond | CH$_2$—CH$_2$ | O (6) |
| 4-Acetyl-phenyl | Isobutyl | Hexyl (7) | Me | Me | O | Bond | CH$_2$—CH$_2$ | S (6) |
| 4-Cyclo-hexylphenyl | Ethyl | Isopropyl (7) | H | H | S | Bond | CH$_2$—CH$_2$ | O (6) |
| (4-NO$_2$) Phenyl | Propyl | 2-Propynyl (7) | Me | Me | S | Bond | CH$_2$—CH$_2$ | O (6) |
| (4-NH$_2$) Phenyl | Hexyl | 2-Butenyl (7) | Me | H | S | NMe | CH$_2$—CH$_2$ | O (6) |
| (4-NMe$_2$) Phenyl | Butyl | 2-Pentenyl (7) | Me | Et | O | Bond | CH$_2$—CH$_2$ | O (6) |
| (3,4,5-Me) Phenyl | Isobutyl | Isobutyl (5) | H | H | NH | Bond | CH$_2$—CH$_2$ | S (6) |
| (3,5-Me,4-OH) Phenyl | Ethyl | t-Butyl (5) | H | H | NMe | Bond | CH$_2$—CH$_2$—CH$_2$ | O (6) |

TABLE 5

| R$^1$ | R$^2$ | R$^3$ (position of substitution) | R$^4$ | R$^5$ | A | X$^1$ | Y | Z (position of substitution) |
|---|---|---|---|---|---|---|---|---|
| (3,4-Cl) Phenyl | Isopropyl | Propyl (4) | H | H | S | Bond | CH$_2$—CH$_2$ | O (5) |
| (3,4-Me) Phenyl | Trifluoro-methyl | Butyl (4) | Me | Me | S | NH—CH$_2$ | CH$_2$—CH$_2$ | S (5) |
| (2,4-F) Phenyl | Isopropyl | Hexyl (4) | Me | H | S | Bond | CH$_2$—CH$_2$ | O (5) |
| (2,3-F) Phenyl | Isopropyl | Isopropyl (4) | Me | Et | O | Bond | CH$_2$—CH$_2$ | O (5) |
| (4-OMe) Phenyl | Benzyl | 2-Propynyl (4) | H | H | NH | Bond | CH$_2$—CH$_2$ | O (5) |
| 4-Acetyl-phenyl | Isopropyl | 2-Butenyl (4) | H | H | NMe | Bond | CH$_2$—CH$_2$ | O (5) |
| 4-Cyclo-hexylphenyl | Isopropyl | 2-Pentenyl (4) | Me | Me | S | Bond | CH$_2$—CH$_2$ | S (5) |

(Typical Compounds 2)

The compounds of the invention wherein $X^2$ is a bond, $B^1$ is N, $B^2$ is O, $R^6$ is H are shown in Tables 6 to 10 (in which $R^1$ is a substituent at the 2nd position of the imidazole, oxazole or thiazole ring, and $R^2$ is a substituent at the 5th position of the imidazole, oxazole or thiazole ring).

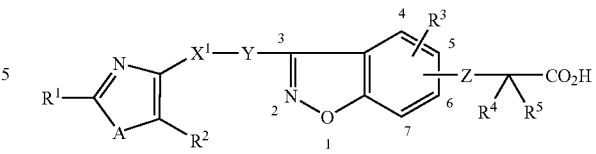

TABLE 6

| $R^1$ | $R^2$ | $R^3$ (position of substitution) | $R^4$ | $R^5$ | A | $X^1$ | Y | Z (position of substitution) |
|---|---|---|---|---|---|---|---|---|
| (2,4-Cl)Phenyl | Isopropyl | Allyl (7) | H | H | O | Bond | CH$_2$—CH$_2$ | O (6) |
| (2,4-Cl)Phenyl | Isopropyl | Allyl (7) | Me | Me | O | Bond | CH$_2$—CH$_2$ | O (6) |
| (2,4-Cl)Phenyl | Isopropyl | Propyl (7) | H | H | O | Bond | CH$_2$—CH$_2$ | O (6) |
| (2-OH,4-Cl)Phenyl | Isopropyl | Propyl (7) | H | H | S | CH(OH) | CH$_2$—CH$_2$ | O (6) |
| (3,4-Me)Phenyl | Isopropyl | Methyl (5, 7) | Me | Me | S | Bond | CH$_2$—CH$_2$ | S (6) |
| (2,4-Me)Phenyl | Isopropyl | Hexyl (7) | Me | H | S | Bond | CH$_2$—CH$_2$ | O (6) |
| (2,3-F)Phenyl | Isopropyl | Isopropyl (7) | Me | Et | O | CO | CH$_2$—CH$_2$ | O (6) |
| (4-OMe)Phenyl | Isopropyl | 2-Propynyl (7)) | H | H | NH | Bond | CH$_2$—CH$_2$ | O (6) |
| 4-Acetyl-phenyl | Isopropyl | 2-Butenyl (7) | H | H | NMe | Bond | CH$_2$—CH$_2$ | O (6) |

TABLE 7

| $R^1$ | $R^2$ | $R^3$ (position of substitution) | $R^4$ | $R^5$ | A | $X^1$ | Y | Z (position of substitution) |
|---|---|---|---|---|---|---|---|---|
| 4-Cyclohexylphenyl | Isopropyl | 2-Pentenyl (7) | Me | Me | S | NHCO | CH$_2$—CH$_2$ | S (6) |
| (4-NO$_2$)Phenyl | Isopropyl | Isobutyl (5) | H | H | S | CONH | CH$_2$—CH$_2$ | O (6) |
| (4-NH$_2$)Phenyl | Isopropyl | t-Butyl (5) | Me | Me | O | Bond | CH$_2$—CH$_2$ | O (6) |
| (4-NMe$_2$)Phenyl | Isopropyl | Allyl (7) | H | H | S | Bond | CH$_2$—CH$_2$ | O (6) |
| (3,4,5-Me)Phenyl | Isopropyl | Methyl (7) | Me | Me | S | CO | CH$_2$—CH$_2$—CH$_2$ | O (6) |
| (3,5-Me,4-OH)Phenyl | Isopropyl | Methyl (5, 7) | Me | H | S | Bond | CH$_2$—CH$_2$ | S (6) |
| 3-Pyridyl | Isopropyl | Propyl (7) | Me | Et | O | Bond | CH$_2$—CH$_2$ | O (6) |
| 2-Pyridyl | Isopropyl | Butyl (7) | H | H | NH | Bond | CH$_2$—CH$_2$ | O (6) |
| 3-Pyridyl | Isopropyl | Hexyl (7) | H | H | NMe | Bond | CH$_2$—CH$_2$ | O (6) |

TABLE 8

| $R^1$ | $R^2$ | $R^3$ (position of substitution) | $R^4$ | $R^5$ | A | $X^1$ | Y | Z (position of substitution) |
|---|---|---|---|---|---|---|---|---|
| 2-Naphthyl | Isopropyl | Isopropyl (7) | Me | Me | S | Bond | CH$_2$—CH$_2$ | O (6) |
| 1-Naphthyl | Isopropyl | 2-Propynyl (7) | H | H | S | Bond | CH$_2$—CH$_2$ | S (6) |
| 2-Quinolyl | Isopropyl | 2-Butenyl (7) | Me | Me | O | Bond | CH$_2$—CH$_2$ | O (6) |
| (4-CF$_3$)Phenyl | Propyl | 2-Pentenyl (7) | H | H | S | NH | CH$_2$—CH$_2$—CH$_2$ | O (6) |
| (4-Cl)Phenyl | Hexyl | Isobutyl (5) | Me | Me | S | Bond | CH$_2$—CH$_2$ | O (6) |
| (4-t-Bu)Phenyl | Butyl | t-Butyl (5) | Me | H | S | Bond | CH$_2$—CH$_2$ | O (6) |
| (3,4-Cl)Phenyl | Isobutyl | Methyl (5, 7) | Me | Et | O | Bond | CH$_2$—CH$_2$ | S (6) |
| (3,4-Me)Phenyl | Ethyl | Methyl (7) | H | H | NH | Bond | CH$_2$—CH$_2$ | O (6) |
| (2,4-F)Phenyl | Propyl | Methyl (5, 7) | H | H | NMe | Bond | CH$_2$—CH$_2$ | O (6) |

TABLE 9

| R¹ | R² | R³ (position of substitution) | R⁴ | R⁵ | A | X¹ | Y | Z (position of substitution) |
|---|---|---|---|---|---|---|---|---|
| (2,3-F) Phenyl | Hexyl | Propyl (7) | Me | Me | S | CH=CH | $CH_2-CH_2$ | O (6) |
| (4-OMe) Phenyl | Butyl | Butyl (7) | H | H | S | Bond | $CH_2-CH_2$ | O (6) |
| 4-Acetyl-phenyl | Isobutyl | Hexyl (7) | Me | Me | O | NMe | $CH_2-CH_2-CH_2$ | S (6) |
| 4-Cyclo-hexylphenyl | Ethyl | Isopropyl (7) | H | H | S | Bond | $CH_2-CH_2$ | O (6) |
| (4-NO₂) Phenyl | Propyl | 2-Propynyl (7) | Me | Me | S | Bond | $CH_2-CH_2$ | O (6) |
| (4-NH₂) Phenyl | Hexyl | 2-Butenyl (7) | Me | H | S | Bond | $CH_2-CH_2$ | O (6) |
| (4-NMe₂) Phenyl | Butyl | 2-Pentenyl (7) | Me | Et | O | Bond | $CH_2-CH_2$ | O (6) |
| (3,4,5-Me) Phenyl | Isobutyl | Isobutyl (5) | H | H | NH | CH(OH) | $CH_2-CH_2-CH_2$ | S (6) |
| (3,5-Me,4-OH) Phenyl | Ethyl | t-Butyl (5) | H | H | NMe | Bond | $CH_2-CH_2$ | O (6) |

TABLE 10

| R¹ | R² | R³ (position of substitution) | R⁴ | R⁵ | A | X¹ | Y | Z (position of substitution) |
|---|---|---|---|---|---|---|---|---|
| (2,4-Cl) Phenyl | Isopropyl | Allyl (4) | H | H | O | Bond | $CH_2-CH_2$ | O (5) |
| (2,4-Cl) Phenyl | Trifluoro-methyl | Allyl (4) | Me | Me | O | Bond | $CH_2-CH_2$ | O (5) |
| (2,4-Cl) Phenyl | Isopropyl | Propyl (4) | H | H | O | Bond | $CH_2-CH_2$ | O (5) |
| (2-OH,4-Cl) Phenyl | Isopropyl | Propyl (4) | H | H | S | Bond | $CH_2-CH_2$ | O (5) |
| (3,4-Me) Phenyl | Benzyl | Methyl (4) | Me | Me | S | Bond | $CH_2-CH_2$ | S (5) |
| (2,4-Me) Phenyl | Isopropyl | Hexyl (4) | Me | H | S | Bond | $CH_2-CH_2$ | O (5) |
| (2,3-F) Phenyl | Isopropyl | Isopropyl (4) | Me | Et | O | Bond | $CH_2-CH_2$ | O (5) |

(Typical Compounds 3)

The compounds of the invention wherein $X^2$ is a bond, $R^6$ is H are shown in Tables 11 to 15 (in which $R^1$ is a substituent at the 2nd position of the imidazole, oxazole or thiazole ring, and $R^2$ is a substituent at the 4th position of the imidazole, oxazole or thiazole ring).

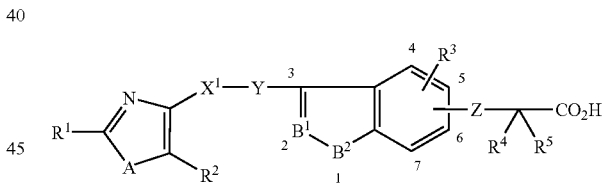

In Tables 11 to 15, (*) means the position of substitution.

TABLE 11

| R¹ | R² | R³ (*) | R⁴ | R⁵ | A | B¹ | B² | X¹ | Y | Z (*) |
|---|---|---|---|---|---|---|---|---|---|---|
| (2,4-Cl) Phenyl | Isopropyl | Allyl (7) | H | H | O | CH | O | Bond | $CH_2-CH_2$ | O (6) |
| (2,4-Cl) Phenyl | Isopropyl | Allyl (7) | Me | Me | O | CH | O | CO | $CH_2-CH_2$ | O (6) |
| (2,4-Cl) Phenyl | Isopropyl | Propyl (7) | H | H | O | CH | S | Bond | $CH_2-CH_2$ | O (6) |
| (2-OH,4-Cl) Phenyl | Isopropyl | Propyl (7) | H | H | S | CH | NH | Bond | $CH_2-CH_2-CH_2$ | O (6) |
| (3,4-Me) Phenyl | Isopropyl | Me (5, 7) | Me | Me | S | N | S | Bond | $CH_2-CH_2$ | S (6) |
| (2,4-Me) Phenyl | Isopropyl | Hexyl (7) | Me | H | S | CH | NMe | CONH | $CH_2-CH_2$ | O (6) |

TABLE 11-continued

| R¹ | R² | R³ (*) | R⁴ | R⁵ | A | B¹ | B² | X¹ | Y | Z (*) |
|---|---|---|---|---|---|---|---|---|---|---|
| (2,3-F)Phenyl | Isopropyl | Isopropyl (7) | Me | Et | O | CH | NPr | Bond | CH₂—CH₂ | O (6) |
| (4-OMe)Phenyl | Isopropyl | 2-Propynyl (7) | H | H | NH | CH | O | CH(OH) | CH₂—CH₂ | O (6) |
| 4-Acetyl-phenyl | Isopropyl | 2-Butenyl (7) | H | H | NMe | CH | O | Bond | CH=CH | O (6) |

TABLE 12

| R¹ | R² | R³ (*) | R⁴ | R⁵ | A | B¹ | B² | X¹ | Y | Z (*) |
|---|---|---|---|---|---|---|---|---|---|---|
| 4-Cyclohexyl-phenyl | Isopropyl | 2-Pentenyl (7) | Me | Me | S | CH | S | Bond | CH₂—CH₂ | S (6) |
| (4-NO₂)Phenyl | Isopropyl | Isobutyl (5) | H | H | S | CH | NH | Bond | CH₂—CH₂ | O (6) |
| (4-NH₂)Phenyl | Isopropyl | t-Butyl (5) | Me | Me | O | N | S | NHCO | CH₂—CH₂ | O (6) |
| (4-NMe₂)Phenyl | Isopropyl | Allyl (7) | H | H | S | CH | NMe | Bond | CH₂—CH₂ | O (6) |
| (3,4,5-Me)Phenyl | Isopropyl | Me (7) | Me | Me | S | CH | NPr | Bond | CH₂—CH₂ | O (6) |
| (3,5-Me,4-OH)Phenyl | Isopropyl | Me (5,7) | Me | H | S | CH | O | CH(OH) | CH₂—CH₂—CH₂ | S (6) |
| 3-Pyridyl | Isopropyl | Propyl (7) | Me | Et | O | CH | O | Bond | CH₂—CH₂ | O (6) |
| 2-Pyridyl | Isopropyl | Butyl (7) | H | H | NH | CH | S | Bond | CH₂—CH₂—CH₂ | O (6) |
| 3-Pyridyl | Isopropyl | Hexyl (7) | H | H | NMe | CH | NH | Bond | CH₂—CH₂ | O (6) |

TABLE 13

| R¹ | R² | R³ (*) | R⁴ | R⁵ | A | B¹ | B² | X¹ | Y | Z (*) |
|---|---|---|---|---|---|---|---|---|---|---|
| 2-Naphthyl | Isopropyl | Isopropyl (7) | Me | Me | S | N | S | CONH | CH₂—CH₂ | O (6) |
| 1-Naphthyl | Isopropyl | 2-Propynyl (7) | H | H | S | CH | NMe | Bond | CH₂—CH₂ | S (6) |
| 2-Quinolyl | Isopropyl | 2-Butenyl (7) | Me | Me | O | CH | NPr | Bond | CH₂—CH₂ | O (6) |
| (4-CF₃)Phenyl | Propyl | 2-Pentenyl (7) | H | H | S | CH | O | Bond | CH₂—CH₂ | O (6) |
| (4-Cl)Phenyl | Hexyl | Isobutyl (7) | Me | Me | S | CH | O | Bond | CH₂—CH₂ | O (6) |
| (4-t-Bu)Phenyl | Butyl | t-Butyl (7) | Me | H | S | CH | S | Bond | CH₂—CH₂ | O (6) |
| (3,4-Cl)Phenyl | Isobutyl | Me (5, 7) | Me | Et | O | CH | NH | Bond | CH₂—CH₂ | S (6) |
| (3,4-Me)Phenyl | Et | Me (7) | H | H | NH | N | S | Bond | CH=CH | O (6) |
| (2,4-F)Phenyl | Propyl | Me (6, 7) | H | H | NMe | CH | NMe | Bond | CH₂—CH₂ | O (6) |

TABLE 14

| R¹ | R² | R³ (*) | R⁴ | R⁵ | A | B¹ | B² | X¹ | Y | Z (*) |
|---|---|---|---|---|---|---|---|---|---|---|
| (2,3-F)Phenyl | Hexyl | Propyl (7) | Me | Me | S | CH | NPr | Bond | CH₂—CH₂ | O (6) |
| (4-OMe)Phenyl | Butyl | Butyl (7) | H | H | S | CH | O | Bond | CH₂—CH₂ | O (6) |
| 4-Acetyl-phenyl | Isobutyl | Hexyl (7) | Me | Me | O | CH | O | Bond | CH₂—CH₂ | S (6) |
| 4-Cyclohexylphenyl | Et | Isopropyl (7) | H | H | S | CH | S | CH(OH) | CH₂—CH₂ | O (6) |
| (4-NO₂)Phenyl | Propyl | 2-Propynyl (7) | Me | Me | S | CH | NH | Bond | CH₂—CH₂ | O (6) |
| (4-NH₂)Phenyl | Hexyl | 2-Butenyl (7) | Me | H | S | N | S | Bond | CH₂—CH₂ | O (6) |
| (4-NMe₂)Phenyl | Butyl | 2-Pentenyl (7) | Me | Et | O | CH | NMe | Bond | CH₂—CH₂ | O (6) |
| (3,4,5-Me)Phenyl | Isobutyl | Isobutyl (7) | H | H | NH | CH | NPr | Bond | CH₂—CH₂ | S (6) |

TABLE 15

| R¹ | R² | R³ (*) | R⁴ | R⁵ | A | B¹ | B² | X¹ | Y | Z (*) |
|---|---|---|---|---|---|---|---|---|---|---|
| (3,5-Me,4-OH) Phenyl | Et | t-Butyl (5) | H | H | NMe | CH | O | NH | CH₂—CH₂—CH₂ | O (6) |
| (2,4-Cl) Phenyl | Isopropyl | Allyl (5) | H | H | O | CH | O | Bond | CH₂—CH₂ | O (6) |
| (2,4-Cl) Phenyl | Trifluoro-ethyl | Allyl (5) | Me | Me | O | CH | S | NMe | CH₂—CH₂—CH₂ | O (6) |
| (2,4-Cl) Phenyl | Benzyl | Propyl (5) | H | H | O | CH | NH | Bond | CH₂—CH₂ | O (6) |
| (2-OH,4-Cl) Phenyl | Isopropyl | Propyl (5) | H | H | S | N | S | Bond | CH₂—CH₂ | O (6) |
| (3,4-Me) Phenyl | Isopropyl | Me (5) | Me | Me | S | CH | NMe | Bond | CH₂—CH₂ | S (6) |
| (2,4-Me) Phenyl | Isopropyl | Hexyl (5) | Me | H | S | CH | NPr | Bond | CH₂—CH₂ | O (6) |
| (2,3-F) Phenyl | Isopropyl | Isopropyl (5) | Me | Et | O | CH | O | Bond | CH₂—CH₂ | O (6) |

(Typical Compounds 4)

The compounds of the invention wherein X² is a bond, R⁶ is H are shown in Tables 16 to 20 (in which R¹ is a substituent at the 2nd position of the imidazole, oxazole or thiazole ring, and R² is a substituent at the 5th position of the imidazole, oxazole or thiazole ring).

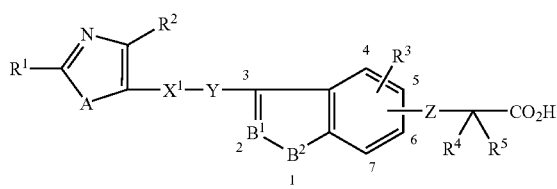

In Tables 16 to 20, (*) means the position of substitution.

TABLE 16

| R¹ | R² | R³ (*) | R⁴ | R⁵ | A | B¹ | B² | X¹ | Y | Z (*) |
|---|---|---|---|---|---|---|---|---|---|---|
| (4-CF₃) Phenyl | Isopropyl | Allyl (7) | Me | Me | S | CH | O | Bond | CH₂—CH₂ | O (6) |
| (4-Cl) Phenyl | Isopropyl | Me (7) | H | H | S | CH | O | Bond | CH₂—CH₂ | O (6) |
| (4-t-Bu) Phenyl | Isopropyl | Me (5, 7) | Me | Me | O | CH | S | CH(OH) | CH₂—CH₂ | O (6) |
| (3,4-Cl) Phenyl | Isopropyl | Propyl (7) | H | H | S | CH | NH | Bond | CH₂—CH₂—CH₂ | O (6) |
| (3,4-Me) Phenyl | Isopropyl | Butyl (7) | Me | Et | S | N | S | Bond | CH=CH | S (6) |
| (2,4-F) Phenyl | Isopropyl | Hexyl (7) | Me | H | S | CH | NMe | Bond | CH₂—CH₂ | O (6) |
| (2,3-F) Phenyl | Isopropyl | Isopropyl (7) | Me | Et | O | CH | NPr | CO | CH₂—CH₂ | O (6) |
| (4-OMe) Phenyl | Isopropyl | 2-Propynyl (7) | H | H | NH | CH | O | Bond | CH₂—CH₂ | O (6) |
| 4-Acetyl-phenyl | Isopropyl | 2-Butenyl (7) | H | H | NMe | CH | O | Bond | CH₂—CH₂ | O (6) |

TABLE 17

| R¹ | R² | R³ (*) | R⁴ | R⁵ | A | B¹ | B² | X¹ | Y | Z (*) |
|---|---|---|---|---|---|---|---|---|---|---|
| 4-Cyclo-hexylphenyl | Isopropyl | 2-Pentenyl (7) | Me | Me | S | CH | S | Bond | CH₂—CH₂ | S (6) |
| (4-NO₂) Phenyl | Isopropyl | Isobutyl (5) | H | H | S | CH | NH | CONH | CH₂—CH₂ | O (6) |
| (4-NH₂) Phenyl | Isopropyl | t-Butyl (5) | Me | Me | O | N | S | Bond | CH₂—CH₂ | O (6) |
| (4-NMe₂) Phenyl | Isopropyl | Allyl (7) | H | H | S | CH | NMe | Bond | CH₂—CH₂ | O (6) |
| (3,4,5-Me) Phenyl | Isopropyl | Me (7) | Me | Me | S | CH | NPr | Bond | CH₂—CH₂ | O (6) |
| (3,5-Me,4-OH) Phenyl | Isopropyl | Me (5, 7) | Me | H | S | CH | O | CO | CH₂—CH₂—CH₂ | S (6) |

TABLE 17-continued

| R¹ | R² | R³ (*) | R⁴ | R⁵ | A | B¹ | B² | X¹ | Y | Z (*) |
|---|---|---|---|---|---|---|---|---|---|---|
| 3-Pyridyl | Isopropyl | Propyl (7) | Me | Et | O | CH | O | Bond | $CH_2-CH_2$ | O (6) |
| 2-Pyridyl | Isopropyl | Butyl (7) | H | H | NH | CH | S | CO | $CH=CH-CH_2-CH_2$ | O (6) |
| 3-Pyridyl | Isopropyl | Hexyl (7) | H | H | NMe | CH | NH | Bond | $CH_2-CH_2$ | O (6) |

TABLE 18

| R¹ | R² | R³ (*) | R⁴ | R⁵ | A | B¹ | B² | X¹ | Y | Z (*) |
|---|---|---|---|---|---|---|---|---|---|---|
| 2-Naphthyl | Isopropyl | Isopropyl (7) | Me | Me | S | N | S | Bond | $CH_2-CH_2$ | O (6) |
| 1-Naphthyl | Isopropyl | 2-Propynyl (7) | H | H | S | CH | NMe | NMe | $CH_2-CH_2-CH_2$ | S (6) |
| 2-Quinolyl | Isopropyl | 2-Butenyl (7) | Me | Me | O | CH | NPr | Bond | $CH_2-CH_2$ | O (6) |
| (4-CF₃) Phenyl | propyl | 2-Pentenyl (7) | H | H | S | CH | O | Bond | $CH_2-CH_2$ | O (6) |
| (4-Cl) Phenyl | Hexyl | Isobutyl (7) | Me | Me | S | CH | O | Bond | $CH_2-CH_2$ | O (6) |
| (4-t-Bu) Phenyl | Butyl | t-Butyl (7) | Me | H | S | CH | S | NMe | $CH_2-CH_2-CH_2$ | O (6) |
| (3,4-Cl) Phenyl | Isobutyl | Allyl (7) | Me | Et | O | CH | NH | Bond | $CH_2-CH_2$ | S (6) |
| (3,4-Me) Phenyl | Et | Me (7) | H | H | NH | N | S | Bond | $CH_2-CH_2$ | O (6) |
| (2,4-F) Phenyl | Propyl | Me (6, 7) | H | H | NMe | CH | NMe | Bond | $CH_2-CH_2$ | O (6) |

TABLE 19

| R¹ | R² | R³ (*) | R⁴ | R⁵ | A | B¹ | B² | X¹ | Y | Z (*) |
|---|---|---|---|---|---|---|---|---|---|---|
| (2,3-F) Phenyl | Hexyl | Propyl (7) | Me | Me | S | CH | NPr | Bond | $CH_2-CH_2$ | O (6) |
| (4-OMe) Phenyl | Butyl | Butyl (7) | H | H | S | CH | O | Bond | $CH_2-CH_2$ | O (6) |
| 4-Acetyl-phenyl | Isobutyl | Hexyl (7) | Me | Me | O | CH | O | Bond | $CH_2-CH_2$ | S (6) |
| 4-Cyclo-hexylphenyl | Et | Isopropyl (7) | H | H | S | CH | S | Bond | $CH_2-CH_2$ | O (6) |
| (4-NO₂) Phenyl | Propyl | 2-Propynyl (7) | Me | Me | S | CH | NH | Bond | $CH_2-CH_2$ | O (6) |
| (4-NH₂) Phenyl | Hexyl | 2-Butenyl (7) | Me | H | S | N | S | CH(OH) | $CH_2-CH_2-CH_2$ | O (6) |
| (4-NMe₂) Phenyl | Butyl | 2-Pentenyl (7) | Me | Et | O | CH | NMe | Bond | $CH_2-CH_2$ | O (6) |
| (3,4,5-Me) Phenyl | Isobutyl | Isobutyl (5) | H | H | NH | CH | NPr | Bond | $CH_2-CH_2$ | S (6) |

TABLE 20

| R¹ | R² | R³ (*) | R⁴ | R⁵ | A | B¹ | B² | X¹ | Y | Z (*) |
|---|---|---|---|---|---|---|---|---|---|---|
| (3,5-Me,4-OH) Phenyl | Et | t-Butyl (5) | H | H | NMe | CH | O | Bond | $CH_2-CH_2$ | O (6) |
| (3,4-Cl) Phenyl | Isopropyl | Propyl (5) | H | H | S | CH | O | Bond | $CH_2-CH_2$ | O (6) |
| (3,4-Me) Phenyl | Trifluoro-methyl | Butyl (5) | Me | Me | S | CH | S | Bond | $CH_2-CH_2$ | S (6) |
| (2,4-F) Phenyl | Benzyl | Hexyl (5) | Me | H | S | CH | NH | Bond | $CH_2-CH_2$ | O (6) |
| (2,3-F) Phenyl | Isopropyl | Isopropyl (5) | Me | Et | O | N | S | Bond | $CH=CH$ | O (6) |
| (4-OMe) Phenyl | Isopropyl | 2-Propynyl (5) | H | H | NH | CH | NMe | Bond | $CH_2-CH_2$ | O (6) |
| 4-Acetyl-phenyl | Isopropyl | 2-Butenyl (4) | H | H | NMe | CH | NPr | Bond | $CH_2-CH_2$ | O (5) |
| 4-Cyclo-hexylphenyl | Isopropyl | 2-Pentenyl (4) | Me | Me | S | CH | O | Bond | $CH_2-CH_2$ | S (5) |

(Typical Compounds 5)

The compounds of the formula (I) wherein A is S, $X^1$ is a bond, $X^2$ is a bond, Y is $CH_2CH_2$, $B^1$ is N, $B^2$ is O, $R^1$ is a substituent at the 2nd position, $R^2$ is a substituent at the 4th position (namely Y is attached to the 5th position) are shown in Tables 21 and 22.

TABLE 21

| $R^1$ | $R^2$ | $R^3$ (position of substitution) | $R^4$ | $R^5$ | Z (position of substitution) |
|---|---|---|---|---|---|
| (4-CF$_3$)Phenyl | Isopropyl | Methyl (5) | H | H | O (6) |
| (4-CF$_3$)Phenyl | Isopropyl | Methyl (5) | Me | Me | O (6) |
| (4-CF$_3$)Phenyl | Isopropyl | Methyl (5) | H | H | S (6) |
| (4-CF$_3$)Phenyl | Isopropyl | Methyl (5) | H | H | NH (6) |
| (4-OCF$_3$)Phenyl | Isopropyl | Methyl (5) | H | H | O (6) |
| (4-OCF$_3$)Phenyl | Isopropyl | Methyl (5) | Me | Me | O (6) |
| (4-Cl)Phenyl | Isopropyl | Methyl (5) | H | H | O (6) |
| (4-Cl)Phenyl | Isopropyl | Methyl (5) | Me | Me | O (6) |
| (4-CF$_3$)Phenyl | Isopropyl | Cl (5) | H | H | S (6) |
| (4-CF$_3$)Phenyl | Isopropyl | Cl (5) | Me | Me | O (6) |
| (4-CF$_3$)Phenyl | Isopropyl | F (5) | H | H | S (6) |
| (4-CF$_3$)Phenyl | Isopropyl | F (5) | Me | Me | O (6) |
| (4-CF$_3$)Phenyl | Isopropyl | Allyl (5) | H | H | O (6) |
| (4-CF$_3$)Phenyl | Isopropyl | Allyl (5) | Me | Me | O (6) |
| (4-CF$_3$)Phenyl | Isopropyl | Ethyl (5) | H | H | O (6) |
| (4-CF$_3$)Phenyl | Isopropyl | Ethyl (5) | Me | Me | S (6) |

TABLE 22

| $R^1$ | $R^2$ | $R^3$ (position of substitution) | $R^4$ | $R^5$ | Z (position of substitution) |
|---|---|---|---|---|---|
| 4-Pyridyl | Isopropyl | Methyl (5) | H | H | O (6) |
| 4-Pyridyl | Isopropyl | Methyl (5) | Me | Me | O (6) |
| (4-Me)Phenyl | Isopropyl | Methyl (5) | H | H | S (6) |
| (4-Me)Phenyl | Isopropyl | Methyl (5) | Me | Me | O (6) |
| (4-Me)Phenyl | Hexyl | Methyl (5) | H | H | O (6) |
| (4-Me)Phenyl | Hexyl | Methyl (5) | Me | Me | O (6) |
| (4-CF$_3$)Phenyl | Hexyl | Methyl (5) | H | H | S (6) |
| (4-CF$_3$)Phenyl | Hexyl | Methyl (5) | Me | Me | O (6) |
| (4-CF$_3$)Phenyl | (4-CF$_3$)Phenethyl | Methyl (5) | H | H | S (6) |
| (4-CF$_3$)Phenyl | (4-CF$_3$)Phenethyl | Methyl (5) | Me | Me | O (6) |
| (4-CF$_3$)Phenyl | Sec-butyl | Methyl (5) | H | H | O (6) |
| (4-CF$_3$)Phenyl | Sec-butyl | Methyl (5) | Me | Me | O (6) |
| (4-CF$_3$)Phenyl | Butyl | Methyl (5) | H | H | O (6) |
| (4-CF$_3$)Phenyl | Butyl | Methyl (5) | Me | Me | O (6) |
| (4-CF$_3$)Phenyl | Ethyl | Methyl (5) | H | H | O (6) |
| (4-CF$_3$)Phenyl | Methyl | Methyl (5) | Me | Me | O (6) |

(Typical Compounds 6)

The compounds of the formula (I) wherein A is O, $R^2$ is isopropyl, $X^1$ is a bond, $X^2$ is a bond, Y is $CH_2CH_2$, $B^1$ is N, $B^2$ is O, $R^1$ is a substituent at the 2nd position, $R^2$ is a substituent at the 5th position (namely Y is attached to the 4th position) are shown in Table 23.

TABLE 23

| $R^1$ | $R^3$ (position of substitution) | $R^4$ | $R^5$ | Z (position of substitution) |
|---|---|---|---|---|
| (2,4-Cl)Phenyl | Methyl (5) | H | H | O (6) |
| (2,4-Cl)Phenyl | Methyl (5) | Me | Me | O (6) |
| (2,4-Cl)Phenyl | Methyl (5) | H | H | S (6) |
| (4-CF$_3$)Phenyl | Methyl (5) | H | H | NH (6) |
| (4-OCF$_3$)Phenyl | Methyl (5) | H | H | O (6) |
| (4-OCF$_3$)Phenyl | Methyl (5) | Me | Me | O (6) |
| (4-CF$_3$)Phenyl | Cl (5) | H | H | S (6) |
| (4-CF$_3$)Phenyl | Cl (5) | Me | Me | O (6) |
| (4-CF$_3$)Phenyl | F (5) | H | H | S (6) |
| (4-CF$_3$)Phenyl | F (5) | Me | Me | O (6) |
| (4-CF$_3$)Phenyl | Allyl (5) | H | H | O (6) |
| (4-CF$_3$)Phenyl | Allyl (5) | Me | Me | O (6) |
| (4-CF$_3$)Phenyl | Ethyl (5) | H | H | O (6) |
| (4-CF$_3$)Phenyl | Ethyl (5) | Me | Me | S (6) |

(Typical Compounds 7)

The compounds of the formula (I) wherein $R^3$ is methyl, which is a substituent at the 5th position, $X^1$ is a bond, $X^2$ is a bond, Y is $CH_2CH_2$, $B^1$ is N, $B^2$ is O, $R^1$ is a substituent at the 2nd position, $R^2$ is a substituent at the 5th position (namely Y is attached to the 4th position) are shown in Table 24.

TABLE 24

| $R^1$ | $R^2$ | $R^4$ | $R^5$ | A | Z (position of substitution) |
|---|---|---|---|---|---|
| 4-Pyridyl | Isopropyl | H | H | O | O (6) |
| 4-Pyridyl | Isopropyl | Me | Me | O | O (6) |
| (4-Me)Phenyl | Isopropyl | H | H | O | S (6) |
| (4-Me)Phenyl | Isopropyl | Me | Me | O | O (6) |
| (4-Me)Phenyl | Hexyl | H | H | O | O (6) |
| (4-Me)Phenyl | Hexyl | Me | Me | O | O (6) |
| (4-CF$_3$)Phenyl | Hexyl | H | H | O | S (6) |
| (4-CF$_3$)Phenyl | Hexyl | Me | Me | O | O (6) |
| (4-CF$_3$)Phenyl | (4-CF$_3$)Phenethyl | H | H | NH | S (6) |
| (4-CF$_3$)Phenyl | (4-CF$_3$)Phenethyl | Me | Me | NMe | O (6) |
| (2-OH, 4-Cl)Phenyl | Isopropyl | H | H | O | O (6) |
| (2-OH, 4-Cl)Phenyl | Isopropyl | Me | Me | O | O (6) |

The pharmacological effects of the invention are described below.

PPARδ transactivation activity of the compound of the invention was measured in the manner described below.

A receptor expression plasmid (GAL4-hPPARδ LBD), a reporter plasmid (UASx4-TK-LUC) and a β-galactosidase (β-GAL) expression plasmid were transfected into CV-1 cells by using DMRIE-C reagent. Subsequently, the cells were incubated for 40 hours in the presence of a compound of the invention, and then the luciferase and β-GAL activities of the cell lysate were assayed.

The luciferase activity was corrected by the β-GAL activity, and a relative transactivation activity was calculated under the condition that the luciferase activity of the cells treated by L-165041 was regarded as 100% (see the below-mentioned Examples 11 and 12).

As shown in Tables 25 and 26, it is clear that the compounds of the invention (Examples 1, 2, 5–10) show selective and potent PPARδ transactivation activities.

Furthermore, it is clear from Table 27 the compound described in Example 6 show a potent HDL cholesterol elevating effect.

Apparently, the compounds of the invention having the general formula (I) show potent PPARδ transactivation activities. Accordingly, these compounds are expected to be useful for prevention and treatment of the following diseases: hyperglycemia, diabetes, insulin resistance, dyslipidemia, hyperlipidemia, obesity, syndrome X, hypercholesterolemia, other dyslipidemia such as hyperlipopreoteinemia, atherosclerosis, diseases of cardiovascular systems, hyperphagia, ischemic diseases, malignant tumors such as lung cancer, mammary cancer, colonic cancer, cancer of great intestine, and ovary cancer, Alzheimer's disease, inflammatory disease, osteoporosis (Mano H. et al., (2000) J. Biol. Chem., 175:8126–8132), Basedow's disease, and adrenal cortical dystrophy.

The compound of the invention can be administered to human by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

For the preparation of these pharmaceuticals, ordinary additives such as vehicles, disintegrators, binders, lubricants, dyes, and diluents. As the vehicles, lactose, D-mannitol, crystalline cellulose and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpirrolidone (PVP) as the binders.

The compound of the invention can be administered to an adult generally in an amount of 0.1 mg to 100 mg a day by parenteral administration and 1 mg to 2,000 mg a day by oral administration. The dosage can be adjusted in consideration of age and conditions of the patient.

The invention is further described by the following non-limiting examples.

EXAMPLES

Example 1

[[7-Allyl-3-[2-[2-(2,4-dichlorophenyl)-5-isopropyl-4-oxazolyl]ethyl]-1,2-benzisoxazol-6-yl]oxy]acetic acid (1) 6-Acetamido-3-[2-[2-(2,4-dichlorophenyl)-5-isopropyl-4-oxazolyl]ethyl]-1,2-benzisoxazole 6-Acetamido-3-methyl-1,2-benzisoxazole (571 mg, 3.00 mmol) was dissolved in dry THF (18 mL). 2M of LDA (3.1 mL, 6.2 mmol) was dropwise added to the solution for 10 minutes under nitrogen atmosphere at −78° C. A solution of 4-iodomethyl-5-isopropyl-2-(2,4-dichlorophenyl)oxazole (1.19 g, 3.00 mmol) in THF (3.0 mL) was dropwise added to the resulting mixture for 7 minutes. The mixture was stirred for 1 hour under the same conditions. The mixture was allowed to room temperature. A saturated aqueous ammonium chloride solution and ethyl acetate were added to the mixture. The organic layer was washed with water and saline, and dried over anhydrous sodium sulfate. Ethyl acetate was removed under reduced pressure. The residue was purified by column chromatography on silica gel with chloroform/methanol (80/1) to give the desired compound (904 mg) as pale yellow oil (yield 70%).

$^1$H-NMR (CDCl$_3$, 400 MHz) δ: 1.10 (d, 6H, J=7 Hz), 2.22 (s, 3H), 2.93 (dq, 1H, J=7 Hz, 7 Hz), 3.06 (t, 2H, J=7 Hz), 3.34 (t, 2H, J=7 Hz), 7.12 (dd, 1H, J=2, 9 Hz), 7.32 (dd, 1H, J=2, 9 Hz), 7.37 (d, 1H, J=2 Hz), 7.43 (d, 1H, J=9 Hz), 7.51 (d, 1H, J=2 Hz), 7.89 (d, 1H, J=9 Hz), 8.05 (s, 1H).

(2) 6-Hydroxy-3-[2-[2-(2,4-dichlorophenyl)-5-isopropyl-4-oxazolyl]ethyl]-1,2-benzisoxazole The obtained 6-acetamido-3-[2-[2-(2,4-dichlorophenyl)-5-isopropyl-4-oxazolyl]ethyl]-1,2-benzisoxazole (900 mg, 1.96 mmol) was reacted in 3N hydrochloric acid (45 mL) at 100° C. for 4 hours. The reaction mixture was allowed to room temperature, neutralized with a saturated aqueous sodium hydrogen carbonate solution, and extracted with ethyl acetate. The organic layer was washed with saline, and dried over anhydrous sodium sulfate. The solvent was removed under reduced pressure to give 6-amino-3-[2-[2-(2,4-dichlorophenyl)-5-isopropyl-4-oxazolyl]ethyl]-1,2-benzisoxazole (770 mg) as brown oil in the residue. The product (770 mg, 1.85 mmol) was suspended in 25% sulfuric acid (9.3 mL), and cooled with ice. An aqueous sodium nitrite solution (166 mg, 2.41 mmol/1.3 ml) was dropwise added to the suspension for 5 minutes. The resulting solution was stirred for 45 minutes under the same conditions. The reaction mixture was dropwise added to a 75% sulfuric acid (7.4 mL) while refluxing for 5 minutes, and the mixture was refluxed for 4 hours. The reaction mixture was left to get cool, extracted with diethyl ether, washed with a saturated aqueous ammonium chloride solution and saline, and dried over anhydrous sodium sulfate. Diethyl ether was removed under reduced pressure. The residue was purified by column chromatography on silica gel with hexane/ethyl acetate (3/1) to give the desired compound (138 mg) as pale yellow oil (yield of the two steps 17%).

$^1$H-NMR (CDCl$_3$, 400 MHz) δ: 1.23 (d, 6H, J=7 Hz), 2.93 (dq, 1H, J=7 Hz, 7 Hz), 3.06 (t, 2H, J=7 Hz), 3.32 (t, 2H, J=7 Hz), 5.36 (s, 1H), 6.75 (dd, 1H, J=2, 8 Hz) 6.92 (d, 1H, J=2 Hz) 7.30 (dd, 1H, J=2, 8 Hz), 7.35 (d, 1H, J=8 Hz), 7.51 (d, 1H, J=2 Hz), 7.89 (d, 1H, J=8 Hz).

(3) 6-Allyloxy-3-[2-[2-(2,4-dichlorophenyl)-5-isopropyl-4-oxazolyl]ethyl]-1,2-benzisoxazole The obtained 6-hydroxy-3-[2-[2-(2,4-dichlorophenyl)-5-isopropyl-4-oxazolyl]ethyl]-1,2-benzisoxazole (500 mg, 1.20 mmol) and potassium carbonate (249 mg, 1.80 mmol) were suspended in acetone (30 mL). Allyl bromide (217 mg, 1.80 mmol) was dropwise added to the suspension for 1 minute while cooling with ice. The mixture was allowed to room temperature, and stirred for 20 hours. After insoluble was filtered off, the filter cake was washed with acetone. The filtrate and washings were combined, and concentrated. The residue was purified by column chromatography on silica gel with hexane/ethyl acetate (4/1) to give the desired compound (420 mg) as colorless oil (yield 77%).

$^1$H-NMR (CDCl$_3$, 400 MHz) δ: 1.11 (d, 6H, J=7 Hz), 2.92 (dq, 1H, J=7 Hz, 7 Hz), 3.06 (t, 2H, J=7 Hz), 3.32 (t, 2H, J=7 Hz), 4.5–4.6 (m, 2H), 5.3–5.5 (m, 2H), 6.0–6.1 (m, 1H), 6.86 (dd, 1H, J=2, 8 Hz) 6.96 (d, 1H, J=2 Hz) 7.32 (dd, 1H, J=2, 8 Hz), 7.36 (d, 1H, J=8 Hz), 7.51 (d, 1H, J=2 Hz), 7.90 (d, 1H, J=8 Hz).

(4) 7-Allyl-6-hydroxy-3-[2-[2-(2,4-dichlorophenyl)-5-isopropyl-4-oxazolyl]ethyl]-1,2-benzisoxazole 6-Allyloxy-3-[2-[2-(2,4-dichlorophenyl)-5-isopropyl-4-oxazolyl]ethyl]-1,2-benzisoxazole (70 mg, 0.153 mmol) was heated at 180° C. for 4 hours. The product was allowed to room temperature, and purified by column chromatography on silica gel with hexane/ethyl acetate (3/1) to give the desired compound (47 mg) as white powder (yield 67%).

¹H-NMR (CDCl₃, 400 MHz) δ: 1.11 (d, 6H, J=7 Hz), 2.92 (dq, 1H, J=7 Hz, 7 Hz), 3.05 (t, 2H, J=7 Hz), 3.31 (t, 2H, J=7 Hz), 3.65–3.70 (m, 2H), 5.15–5.25 (m, 2H), 5.41 (s, 1H), 6.0–6.1 (m, 1H), 6.76 (d, 1H, J=8 Hz), 7.25 (d, 1H, J=8 Hz) 7.32 (dd, 1H, J=2, 8 Hz), 7.51 (d, 1H, J=2 Hz), 7.89 (d, 1H, J=8 Hz).

(5) Ethyl [[7-allyl-3-[2-[2-(2,4-dichlorophenyl)-5-isopropyl-4-oxazolyl]ethyl]-1,2-benzisoxazol-6-yl]oxy]acetate The obtained 7-allyl-6-hydroxy-3-[2-[2-(2,4-dichlorophenyl)-5-isopropyl-4-oxazolyl]ethyl]-1,2-benzisoxazole (45 mg, 0.098 mmol) and potassium carbonate (20 mg, 0.147 mmol) was suspended in acetone (5.0 mL). An acetone solution of ethyl bromoacetate (25 mg, 0.147 mmol) was added to the suspension while cooling with ice. The mixture was allowed to room temperature, and stirred for 20 hours. After insoluble was filtered off, the filter cake was washed with acetone. The filtrate and washings were combined, and concentrated. The residue was purified by column chromatography on silica gel with hexane/ethyl acetate (4/1) to give the desired compound (43 mg) as colorless oil (yield 80%).

¹H-NMR (CDCl₃, 400 MHz) δ: 1.11 (d, 6H, J=7 Hz), 1.28 (t, 3H, J=7 Hz), 2.91 (dq, 1H, J=7 Hz, 7 Hz), 3.05 (t, 2H, J=7 Hz), 3.32 (t, 2H, J=7 Hz), 3.65–3.70 (m, 2H), 4.25 (q, 2H, J=7 Hz) 4.70 (s, 2H) 4.95–5.15 (m, 2H), 6.0–6.1 (m, 1H), 6.74 (d, 1H, J=9 Hz), 7.30 (d, 1H, J=9 Hz) 7.32 (dd, 1H, J=2, 9 Hz), 7.51 (d, 1H, J=2 Hz), 7.89 (d, 1H, J=9 Hz).

(6) [[7-Allyl-3-[2-[2-(2,4-dichlorophenyl)-5-isopropyl-4-oxazolyl]ethyl]-1,2-benzisoxazol-6-yl]oxy]acetic acid The obtained ester compound (40 mg, 0.074 mmol) was dissolved in an ethanol-water (3.0 mL–1.5 mL). Lithium hydroxide Monohydrate of (8 mg) was added to the solution, and the mixture was stirred for 20 hours. Ice was added to the reaction mixture. The mixture was neutralized with 3N hydrochloric acid. The crystals were filtered, washed with water, air-dried over night, and further dried under reduced pressure to give the desired compound (25 mg) as white powder (yield 66%). mp 80–85° C.

¹H-NMR (CDCl₃, 400 MHz) δ: 1.13 (d, 6H, J=7 Hz), 2.94 (dq, 1H, J=7 Hz, 7 Hz), 3.06 (t, 2H, J=7 Hz), 3.31 (t, 2H, J=7 Hz), 3.65–3.75 (m, 2H), 4.73 (s, 2H) 5.0–5.2 (m, 2H), 5.9–6.1 (m, 1H), 6.76 (d, 1H, J=9 Hz), 7.32 (d, 1H, J=9 Hz) 7.32 (dd, 1H, J=2, 9 Hz), 7.51 (d, 1H, J=2 Hz), 7.89 (d, 1H, J=9 Hz).

Example 2

2-[[7-Allyl-3-[2-[2-(2,4-dichlorophenyl)-5-isopropyl-4-oxazolyl]ethyl]-1,2-benzisoxazol-6-yl]oxy]-2-methylpropionic acid (1) Ethyl 2-[[7-allyl-3-[2-[2-(2,4-dichlorophenyl)-5-isopropyl-4-oxazolyl]ethyl]-1,2-benzisoxazol-6-yl]oxy]-2-methylpropionate 7-Allyl-6-hydroxy-3-[2-[2-(2,4-dichlorophenyl)-5-isopropyl-4-oxazolyl]ethyl]-1,2-benzisoxazole (92 mg, 0.20 mmol), ethyl 2-bromo-2-methylpropionate (196 mg, 1.00 mmol) and potassium carbonate (138 mg, 1.00 mmol) were suspended in methyl ethyl ketone (5.0 mL). The suspension was refluxed for 20 hours, and allowed to room temperature. After insoluble was filtered off, the filter cake was washed with methyl ethyl ketone. The filtrate and washings were combined, and concentrated. The residue was purified by column chromatography on silica gel with hexane/ethyl acetate (5/1) to give the desired compound (100 mg) as colorless oil (quantitative yield).

¹H-NMR (CDCl₃, 400 MHz) δ: 1.09 (d, 6H, J=7 Hz), 1.23 (t, 3H, J=7 Hz), 1.60 (s, 6H), 2.90 (dq, 1H, J=7 Hz, 7 Hz), 3.04 (t, 2H, J=7 Hz), 3.31 (t, 2H, J=7 Hz), 3.65–3.70 (m, 2H), 4.23 (q, 2H, J=7 Hz), 4.95–5.15 (m, 2H), 6.0–6.1 (m, 1H), 6.65 (d, 1H, J=9 Hz), 7.19 (d, 1H, J=9 Hz), 7.32 (dd, 1H, J=2, 9 Hz), 7.51 (d, 1H, J=2 Hz), 7.89 (d, 1H, J=9 Hz).

(2) 2-[[7-Allyl-3-[2-[2-(2,4-dichlorophenyl)-5-isopropyl-4-oxazolyl]ethyl]-1,2-benzisoxazol-6-yl]oxy]-2-methylpropionic acid The desired compound was obtained in an analogous manner as in (6) of Example 1 (yield 73%).

¹H-NMR (CDCl₃, 400 MHz) δ: 1.10 (d, 6H, J=7 Hz), 1.63 (s, 6H), 2.92 (dq, 1H, J=7 Hz, 7 Hz), 3.06 (t, 2H, J=7 Hz), 3.31 (t, 2H, J=7 Hz), 3.65–3.70 (m, 2H), 5.00–5.15 (m, 2H), 5.9–6.1 (m, 1H), 6.80 (d, 1H, J=8 Hz), 7.21 (d, 1H, J=8 Hz), 7.30 (dd, 1H, J=2, 8 Hz), 7.49 (d, 1H, J=2 Hz), 7.85 (d, 1H, J=8 Hz).

Example 3

[[7-Propyl-3-[2-[2-(2,4-dichlorophenyl)-5-isopropyl-4-oxazolyl]ethyl]-1,2-benzisoxazol-6-yl]oxy]acetic acid (1) Ethyl [[7-propyl-3-[2-[2-(2,4-dichlorophenyl)-5-isopropyl-4-oxazolyl]ethyl]-1,2-benzisoxazol-6-yl]oxy]acetate Ethyl [[7-allyl-3-[2-[2-(2,4-dichlorophenyl)-5-isopropyl-4-oxazolyl]ethyl]-1,2-benzisoxazol-6-yl]oxy]acetate (65 mg, 0.12 mmol) was dissolved in ethanol (7.0 mL). To the solution, 10% Pd—C (6 mg) was added. The mixture was stirred for 3 hours under hydrogen atmosphere (and ordinary pressure). After insoluble was filtered off, the filtrate was condensed to give the desired compound (63 mg) as colorless oil in the residue (yield 97%).

¹H-NMR (CDCl₃, 400 MHz) δ: 0.97 (t, 3H, J=7 Hz), 1.09 (d, 6H, J=7 Hz), 1.26 (t, 3H, J=7 Hz), 1.7–1.8 (m, 2H), 2.9–3.0 (m, 3H), 3.05 (t, 2H, J=7 Hz), 3.32 (t, 2H, J=7 Hz), 4.25 (q, 2H, J=7 Hz), 4.70 (s, 2H), 6.71 (d, 1H, J=8 Hz), 7.25 (d, 1H, J=9 Hz), 7.33 (dd, 1H, J=2, 9 Hz), 7.51 (d, 1H, J=2 Hz), 7.89 (d, 1H, J=8 Hz).

(2) [[7-Propyl-3-[2-[2-(2,4-dichlorophenyl)-5-isopropyl-4-oxazolyl]ethyl]-1,2-benzisoxazol-6-yl]oxy]acetic acid The desired compound was obtained in an analogous manner as in (6) of Example 1.

¹H-NMR (CDCl₃, 400 MHz) δ: 0.96 (t, 3H, J=7 Hz), 1.12 (d, 6H, J=7 Hz), 1.7–1.8 (m, 2H), 2.9–3.0 (m, 3H), 3.06 (t, 2H, J=7 Hz), 3.30 (t, 2H, J=7 Hz), 4.25 (q, 2H, J=7 Hz), 4.74 (s, 2H), 6.74 (d, 1H, J=8 Hz), 7.26 (d, 1H, J=9 Hz), 7.33 (dd, 1H, J=2, 9 Hz), 7.51 (d, 1H, J=2 Hz), 7.87 (d, 1H, J=8 Hz).

Example 4

2-[[7-Allyl-3-[2-[2-[(4-trifluoromethyl)phenyl]-4-isopropyl-5-thiazolyl]ethyl]-1,2-benzisoxazol-6-yl]oxy]-2-methylpropionic acid The following (1) to (5) were conducted in an analogous manner as in Example 1, and the following (6) and (7) were conducted in an analogous manner as in Example 2.

(1) 6-Acetamido-3-[2-[2-[(4-trifluoromethyl)phenyl]-4-isopropyl-5-thiazolyl]ethyl]-1,2-benzisoxazole Pale yellow oil Yield 20%

$^1$H-NMR (CDCl$_3$, 400 MHz) δ: 1.24 (d, 6H, J=7 Hz), 2.23 (s, 3H), 3.03 (dq, 1H, J=7 Hz, 7 Hz), 3.25–3.40 (m, 4H), 7.20 (dd, 1H, J=2, 9 Hz), 7.36 (d, 1H, J=2 Hz), 7.44 (d, 1H, J=9 Hz), 7.65 (d, 2H, J=8 Hz), 7.99 (d, 2H, J=8 Hz), 8.07 (s, 1H).

(2) 6-Amino-3-[2-[2-[(4-trifluoromethyl)phenyl]-4-isopropyl-5-thiazolyl]ethyl]-1,2-benzisoxazole Pale yellow oil Yield 93%

$^1$H-NMR (CDCl$_3$, 400 MHz) δ: 1.25 (d, 6H, J=7 Hz), 3.04 (dq, 1H, J=7 Hz, 7 Hz), 3.15–3.40 (m, 4H), 4.0–4.05 (br, 2H), 6.61 (dd, 1H, J=2, 9 Hz), 6.73 (d, 1H, J=2 Hz), 7.27 (d, 1H, J=9 Hz), 7.65 (d, 2H, J=8 Hz), 8.00 (d, 2H, J=8 Hz), (3) 6-Hydroxy-3-[2-[2-[(4-trifluoromethyl)phenyl]-4-isopropyl-5-thiazolyl]ethyl]-1,2-benzisoxazole Pale yellow oil Yield 32%

$^1$H-NMR (CDCl$_3$, 400 MHz) δ: 1.24 (d, 6H, J=7 Hz), 3.03 (dq, 1H, J=7 Hz, 7 Hz), 3.2–3.4 (m, 4H), 5.95–6.00 (br, 1H), 6.83 (dd, 1H, J=2, 9 Hz), 6.79 (d, 1H, J=2 Hz), 7.38 (d, 1H, J=9 Hz), 7.64 (d, 2H, J=8 Hz), 7.99 (d, 2H, J=8 Hz).

(4) 6-Allyloxy-3-[2-[2-[(4-trifluoromethyl)phenyl]-4-isopropyl-5-thiazolyl]ethyl]-1,2-benzisoxazole Pale yellow oil Yield 49%

$^1$H-NMR (CDCl$_3$, 400 MHz) δ: 1.24 (d, 6H, J=7 Hz), 3.04 (dq, 1H, J=7 Hz, 7 Hz), 3.2–3.4 (m, 4H), 4.60–4.65 (m, 2H), 5.30–5.50 (m, 2H), 6.00–6.15 (m, 1H), 6.93 (dd, 1H, J=2, 9 Hz), 7.00 (d, 1H, J=2 Hz), 7.40 (d, 1H, J=9 Hz), 7.65 (d, 2H, J=8 Hz), 8.00 (d, 2H, J=8 Hz).

(5) 7-Allyloxy-6-hydroxy-3-[2-[2-[(4-trifluoromethyl)phenyl]-4-isopropyl-5-thiazolyl]ethyl]-1,2-benzisoxazole White powder Yield 71%

$^1$H-NMR (CDCl$_3$, 400 MHz) δ: 1.24 (d, 6H, J=7 Hz), 3.03 (dq, 1H, J=7 Hz, 7 Hz), 3.2–3.4 (m, 4H), 3.65–3.75 (m, 2H), 5.15–5.30 (m, 2H), 5.56 (s, 1H), 6.00–6.10 (m, 1H), 6.84 (d, 1H, J=9 Hz), 7.28 (d, 1H, J=9 Hz), 7.65 (d, 2H, J=8 Hz), 8.00 (d, 2H, J=8 Hz).

(6) Ethyl 2-[[7-allyl-3-[2-[2-[(4-trifluoromethyl)phenyl]-4-isopropyl-5-thiazolyl]ethyl]-1,2-benzisoxazol-6-yl]oxy]-2-methylpropionate Pale yellow oil Yield 48%

$^1$H-NMR (CDCl$_3$, 400 MHz) δ: 1.23 (t, 3H, J=7 Hz), 1.23 (d, 6H, J=7 Hz), 1.62 (s, 6H), 3.02 (dq, 1H, J=7 Hz, 7 Hz), 3.2–3.4 (m, 4H), 3.65–3.75 (m, 2H), 4.23 (q, 2H, J=7 Hz), 5.0–5.15 (m, 2H), 5.95–6.10 (m, 1H), 6.71 (d, 1H, J=9 Hz), 7.22 (d, 1H, J=9 Hz), 7.65 (d, 2H, J=8 Hz), 7.99 (d, 2H, J=8 Hz).

(7) 2-[[7-Allyl-3-[2-[2-[(4-trifluoromethyl)phenyl]-4-isopropyl-5-thiazolyl]ethyl]-1,2-benzisoxazol-6-yl]oxy]-2-methylpropionic acid Colorless oil Yield 81%

$^1$H-NMR (CDCl$_3$, 400 MHz) δ: 1.23 (d, 6H, J=7 Hz), 1.65 (s, 6H), 3.01 (dq, 1H, J=7 Hz, 7 Hz), 3.2–3.4 (m, 4H), 3.65–3.75 (m, 2H), 5.0–5.15 (m, 2H), 5.95–6.10 (m, 1H), 6.85 (d, 1H, J=9 Hz), 7.27 (d, 1H, J=9 Hz), 7.65 (d, 2H, J=8 Hz), 7.99 (d, 2H, J=8 Hz).

Example 5

[3-[2-[4-Isopropyl-2-(4-trifluoromethyl)phenyl-5-thiazolyl]-ethyl]-5-methyl-1,2-benzisoxazol-6-yl] oxyacetic acid (1) 6-Acetamido-3-[2-[4-isopropyl-2-(4-trifluoromethyl)phenyl-5-thiazolyl]ethyl]-5-methyl-1,2-benzisoxazole 6-Acetamido-3,5-dimethyl-1,2-benzisoxazole (9.18 g, 45.0 mmol) was dissolved in dry THF (315 mL). To the solution, 2M LDA (53 mL, 106.0 mmol) was dropwise added for 40 minutes at −78° C. under nitrogen atmosphere, and the mixture was stirred for 15 minutes at the same conditions (at −78° C.), to which THF solution (100 mL) of 4-isopropyl-5-iodomethyl-2-(4-trifluoromethyl)phenylthiazole (18.51 g, 45.0 mmol) was dropwise added for 45 minutes. The mixture was stirred for 1 hour under the same conditions (at −78° C.), and allowed to room temperature. A saturated aqueous ammonium chloride solution and ethyl acetate were added to reaction the mixture. The ethyl acetate layer was washed with water and saline, dried over anhydrous sodium sulfate. After ethyl acetate was removed, the residue was purified by column chromatography on silica gel with hexane/ethyl acetate (1/1) to give the desired compound (7.40 g) as pale yellow crystals (yield 34%).

$^1$H-NMR (CDCl$_3$, 400 MHz) δ: 1.25 (d, 6H, J=7 Hz), 2.26 (bs, 3H), 2.32 (s, 3H), 3.04 (m, 1H), 3.26 (dd, 2H, J=6, 8 Hz), 3.37 (dd, 2H, J=6, 8 Hz), 7.12 (bs, 1H), 7.65 (d, 2H, J=8 Hz), 7.99 (d, 2H, J=8 Hz), 8.40 (bs, 1H).

(2) 6-Amino-3-[2-[4-isopropyl-2-(4-trifluoromethyl)phenyl-5-thiazolyl]ethyl]-5-methyl-1,2-benzisoxazole The obtained amide compound (18.0 g, 36.9 mmol) was suspended in 4M hydrochloric acid (360 mL) and acetic acid (180 mL). The suspension was refluxed for 24 hours, allowed to room temperature, poured in to ice-cold water, and neutralized with 10N aqueous sodium hydroxide solution. After ethyl acetate was added to the mixture, the organic layer was washed with saline, dried over anhydrous sodium sulfate. After the solvent was removed, the crude crystal in the residue was filtered, washed with hexane to give the desired compound (16.8 g) as pale brown crystal (yield 94%).

$^1$H-NMR (CDCl$_3$, 400 MHz) δ: 1.25 (d, 6H, J=7 Hz), 2.21 (s, 3H), 3.05 (m, 1H), 3.21 (dd, 2H, J=6, 9 Hz), 3.35 (dd, 2H, J=6, 9 Hz), 4.01 (bs, 2H), 6.75 (s, 1H), 7.14 (s, 1H), 7.64 (d, 2H, J=8 Hz), 8.00 (d, 2H, J=8 Hz).

(3) 6-Hydroxy-3-[2-[4-isopropyl-2-(4-trifluoromethyl)phenyl-5-thiazolyl]ethyl]-5-methyl-1,2-benzisoxazole The obtained amine compound (15.4 g, 34.6 mmol) was suspended in 25% sulfuric acid (170 ml). An aqueous sodium nitrite solution (3.10 g, 45 mmol) was added to the suspension while cooling with ice. The mixture was stirred for 20 minutes under the same conditions, and dropwise added to 75% sulfuric acid heated at 130° C. The mixture was refluxed for 3 hours under the same conditions, allowed to room temperature, and poured into ice-cold water. After ethyl acetate were added to the mixture, the organic layer was dried over anhydrous sodium sulfate. After the solvent was removed, the crude crystal in the residue was filtered, and washed with hexane to give the desired compound (8.36 g) as pale brown crystals (yield 54%).

$^1$H-NMR (CDCl$_3$, 400 MHz) δ: 1.24 (d, 6H, J=7 Hz), 2.30 (s, 3H), 3.04 (m, 1H), 3.2–3.4 (m, 4H), 5.31 (s, 1H), 6.93 (s, 1H), 7.22 (s, 1H), 7.65 (d, 2H, J=9 Hz), 8.00 (d, 2H, J=9 Hz).

(4) Ethyl [3-[2-[4-isopropyl-2-(4-trifluoromethyl)phenyl-5-thiazolyl]ethyl]-5-methyl-1,2-benzisoxazol-6-yl]oxyacetate The desired compound was obtained in an analogous manner as in (5) of Example 1.

White powder
Yield 65%
$^1$H-NMR (CDCl$_3$, 400 MHz) δ: 1.25 (d, 6H, J=7 Hz), 1.31 (t, 3H, J=7 Hz), 2.33 (s, 3H), 3.04(m, 1H), 3.2–3.4(m, 4H), 4.12(q, 2H, J=7 Hz) 4.71 (s, 2H), 6.83 (s, 1H), 7.25 (s, 1H), 7.65 (d, 2H, J=9 Hz), 8.00 (d, 2H, J=9 Hz).

(5) [3-[2-[4-Isopropyl-2-(4-trifluoromethyl)phenyl-5-thiazolyl]ethyl]-5-methyl-1,2-benzisoxazol-6-yl]oxyacetic acid The desired compound was obtained in an analogous manner as in (6) of Example 1.

White powder
Yield 71%
mp (dec) 180–190° C.
$^1$H-NMR (CDCl$_3$, 400 MHz) δ: 1.24 (d, 6H, J=7 Hz), 2.33 (s, 3H), 3.03 (m, 1H), 3.2–3.4 (m, 4H), 4.77 (s, 2H), 6.87 (s, 1H), 7.26 (s, 1H), 7.64 (d, 2H, J=9 Hz), 7.99 (d, 2H, J=9 Hz).
IR(KBr)cm$^{-1}$: 2960, 2930, 1740, 1620, 1520, 1450, 1420, 1320, 1280, 1250, 1160, 1120, 1060, 840.

Example 6

2-[[3-[2-[4-Isopropyl-2-(4-trifluoromethyl)phenyl-5-thiazolyl]ethyl]-5-methyl-1,2-benzisoxazol-6-yl]oxy]-2-methylpropionic acid (1) Ethyl 2-[[3-[2-[4-isopropyl-2-(4-trifluoromethyl)phenyl-5-thiazolyl]ethyl]-5-methyl-1,2-benzisoxazol-6-yl]oxy]-2-methylpropionate The desired compound was obtained in an analogous manner as in (1) of Example 2.

Pale yellow oil
Yield 85%
$^1$H-NMR (CDCl$_3$, 400 MHz) δ: 1.23 (d, 6H, J=7 Hz), 1.24 (t, 3H, J=7 Hz), 1.67 (s, 6H) 2.26 (s, 3H), 3.02 (m, 1H), 3.2–3.4 (m, 4H), 4.25 (q, 2H, J=7 Hz) 6.77 (s, 1H), 7.25 (s, 1H), 7.65 (d, 2H, J=9 Hz), 8.00 (d, 2H, J=9 Hz).

(2) 2-[[3-[2-[4-Isopropyl-2-(4-trifluoromethyl)phenyl-5-thiazolyl]ethyl]-5-methyl-1,2-benzisoxazol-6-yl]oxy]-2-methylpropionic acid The desired compound was obtained in an analogous manner as in (2) of Example 2.

White crystal
Yield 94%
mp (dec) 166–168° C.
$^1$H-NMR (CDCl$_3$, 400 MHz) δ: 1.23 (d, 6H, J=7 Hz), 1.72 (s, 6H) 2.28 (s, 3H), 3.02 (m, 1H), 3.2–3.4 (m, 4H), 6.93 (s, 1H), 7.25 (s, 1H), 7.65 (d, 2H, J=9 Hz), 8.00 (d, 2H, J=9 Hz).
IR(KBr)cm$^{-1}$: 3000, 1720, 1620, 1520, 1450, 1370, 1320, 1280, 1160, 1120, 1060, 850, 820.

Example 7

[3-[2-[4-Isopropyl-2-(4-trifluoromethyl)phenyl-5-thiazolyl]ethyl]-5-methyl-1,2-benzisoxazol-6-yl]thioacetic acid (1) 3-[2-[4-Isopropyl-2-(4-trifluoromethyl)phenyl-5-thiazolyl]-ethyl]-6-mercapto5-methyl-1,2-benzisoxazole 6-Amino-3-[2-[isopropyl-2-(4-trifluoromethyl)phenyl-5-thiazolyl]ethyl]-5-methyl-1,2-benzisoxazole (475 mg, 1.07 mmol) was dissolved in ethanol (3.3 mL). Concentrated hydrochloric acid (1.68 mL) was added to the solution while cooling with ice (external temperature 0° C.). Sodium nitrite (81 mg, 1.17 mmol) was added to the mixture. An aqueous potassium xanthogenate solution (430 mg, 2.68 mmol) was dropwise added to the mixture for 5 minutes. The interreact temperature was kept at 45° C., and the mixture was stirred for 18 hours. The mixture was left to get cool, poured into water, and extracted with ethyl acetate. The organic layer was washed with saline, dried over anhydrous sodium sulfate. After the solvent was removed, the residue was purified by column chromatography on silica gel with hexane/ethyl acetate (5/1) to give crude dithiocarbonic ester compound (131 mg). The dithiocarbonic ester compound was dissolved in ethanol. An aqueous solution of sodium hydroxide (36 mg) was added to the solution at room temperature. The mixture was refluxed for 3 hours. The reaction mixture was poured into ice-cold water, and neutralized with 1 M hydrochloric acid. After ethyl acetate was added to the mixture, the organic layer was washed with saline, dried over anhydrous sodium sulfate. After the solvent was removed, the residue was purified by column chromatography on silica gel with hexane/ethyl acetate (5/1) to give the desired compound (65 mg) (yield of the two steps 7%).
$^1$H-NMR (CDCl$_3$, 400 MHz) δ: 1.23 (d, 6H, J=7 Hz), 2.38 (s, 3H), 3.04 (m, 1H), 3.2–3.4 (m, 4H), 3.60 (s, 1H), 7.26 (s, 1H), 7.49 (s, 1H) 7.65 (d, 2H, J=9 Hz), 8.00 (d, 2H, J=9 Hz).

(2) Ethyl [[3-[2-[4-isopropyl-2-(4-trifluoromethyl)phenyl-5-thiazolyl]ethyl]-5-methyl-1,2-benzisoxazol-6-yl]thio]acetate The desired compound was obtained in an analogous manner as in (5) of Example 1.

Pale yellow oil
Yield 69%
$^1$H-NMR (CDCl$_3$, 400 MHz) δ: 1.25 (d, 6H, J=7 Hz), 1.27 (t, 3H, J=7 Hz), 2.41 (s, 3H), 3.03 (m, 1H), 3.2–3.4 (m, 4H), 3.76 (s, 2H), 4.22(q, 2H, J=7 Hz) 7.27 (s, 1H), 7.45 (s, 1H), 7.65 (d, 2H, J=9 Hz), 7.99 (d, 2H, J=9 Hz).

(3) [3-[2-[4-Isopropyl-2-(4-trifluoromethyl)phenyl-5-thiazolyl]ethyl]-5-methyl-1,2-benzisoxazol-6-yl]thioacetic acid The desired compound was obtained in an analogous manner as in (6) of Example 1.

Pale yellowish white powder
Yield 73%
mp (dec) 170° C.
$^1$H-NMR (CDCl$_3$, 400 MHz) δ: 1.24 (d, 6H, J=7 Hz), 2.42 (s, 3H), 3.03 (m, 1H), 3.2–3.4 (m, 4H), 3.81 (s, 2H), 7.28 (s, 1H), 7.46 (s, 1H), 7.65 (d, 2H, J=9 Hz), 8.00 (d, 2H, J=9 Hz).

Example 8

[3-[2-[4-Isopropyl-2-(4-trifluoromethyl)phenyl-5-thiazolyl]ethyl]-5-methyl-1,2-benzisoxazol-6-yl]aminoacetic acid (1) Ethyl [3-[2-[4-isopropyl-2-(4-trifluoromethyl)phenyl-5-thiazolyl]ethyl]-5-methyl-1,2-benzisoxazol-6-yl]aminoacetate 6-Amino-3-[2-[4-isopropyl-2-(4-trifluoromethyl)phenyl-5-thiazolyl]ethyl]-5-methyl-1,2-benzisoxazole (445 mg, 1.00 mmol), ethyl bromoacetate (154 mg, 1.20 mmol), diisopropylethylamine (142 mg, 1.10 mmol) were dissolved in DMF (10 mL). The solution was refluxed for 18 hours, poured into water, and extracted with ethyl acetate. The organic layer was washed with saline, dried over anhydrous sodium sulfate. After the solvent was removed, the residue was purified by column chromatography on silica gel with hexane/ethyl acetate (3/1) to give the desired compound (160 mg) as a dark brown powder (yield 30%).

$^1$H-NMR (CDCl$_3$, 400 MHz) δ: 1.25 (d, 6H, J=7 Hz), 1.34 (t, 3H, J=7 Hz), 2.25 (s, 3H), 3.05 (m, 1H), 3.2–3.3 (m, 4H), 3.97 (d, 2H, J=3 Hz) 4.6–4.7 (br, 1H) 4.12 (q, 2H, J=7 Hz) 6.51 (s, 1H), 7.15 (s, 1H), 7.64 (d, 2H, J=9 Hz), 8.00 (d, 2H, J=9 Hz).

(2) 3-[2-[4-Isopropyl-2-(4-trifluoromethyl)phenyl-5-thiazolyl]ethyl]-5-methyl-1,2-benzisoxazol-6-yl]aminoacetic acid The desired compound was obtained in an analogous manner as in (6) of Example 1.

Pale brown crystal
  Yield 73%
  mp (dec) 180–185° C.
  $^1$H-NMR (CDCl$_3$, 400 MHz) δ: 1.25 (d, 6H, J=7 Hz), 2.25 (s, 3H), 3.04 (m, 1H), 3.2–3.3 (m, 4H), 4.07 (s, 2H), 6.54 (s, 1H), 7.15 (s, 1H), 7.64 (d, 2H, J=9 Hz), 7.99 (d, 2H, J=9 Hz).
  IR(KBr)cm$^{-1}$: 3425, 2950, 2925, 1740, 1620, 1520, 1440, 1380, 1370, 1320, 1220, 1160, 1060, 840.

Example 9

[3-[2-[2-(2,4-Dichlorophenyl)-5-isopropyl-4-oxazolyl]ethyl]-5-methyl-1,2-benzisoxazol-6-yl]oxyacetic acid (1) 6-Acetamido-3-[2-[2-(2,4-dichlorophenyl)-5-isopropyl-4-oxazolyl]ethyl]-5-methyl-1,2-benzisoxazole The desired compound was obtained in an analogous manner as in (1) of Example 5.

Brown oil
  Yield 34%
  $^1$H-NMR (CDCl$_3$, 400 MHz) δ: 1.10 (d, 6H, J=7 Hz), 2.24 (bs, 3H), 2.26 (s, 3H), 2.92 (m, 1H), 3.05 (t, 2H, J=7 Hz), 3.33 (t, 2H, J=7 Hz), 7.16 (bs, 1H), 7.28 (s, 1H), 7.32 (dd, 1H, J=2, 9 Hz), 7.51 (d, 1H, J=2 Hz), 7.91 (d, 1H, J=9 Hz), 8.34 (bs, 1H).

(2) 6-Amino-3-[2-[2-(2,4-dichlorophenyl)-5-isopropyl-4-oxazolyl]ethyl]-5-methyl-1,2-benzisoxazole The desired compound was obtained in an analogous manner as in (2) of Example 5.

Yield 42%
  $^1$H-NMR (CDCl$_3$, 400 MHz) δ: 1.10 (d, 6H, J=7 Hz), 2.14 (s, 3H), 2.92 (m, 1H), 3.03 (t, 2H, J=7 Hz), 3.27 (t, 2H, J=7 Hz), 3.97 (bs, 2H), 6.72 (s, 1H), 7.13 (s, 1H), 7.32 (dd, 1H, J=2, 8 Hz), 7.51 (d, 1H, J=2 Hz), 7.92 (d, 1H, J=8 Hz).

(3) 3-[2-[2-(2,4-Dichlorophenyl)-5-isopropyl-4-oxazolyl]ethyl]-6-hydroxy-5-methyl-1,2-benzisoxazole The desired compound was obtained in an analogous manner as in (3) of Example 5.

Pale yellow crystal
  Yield 44%
  $^1$H-NMR (CDCl$_3$, 400 MHz) δ: 1.11 (d, 6H, J=7 Hz), 2.22 (s, 3H), 2.92 (m, 1H), 3.05 (t, 2H, J=7 Hz), 3.29 (t, 2H, J=7 Hz), 6.15 (bs, 1H), 6.88 (s, 1H), 7.19 (s, 1H), 7.32 (dd, 1H, J=2, 9 Hz), 7.51 (d, 1H, J=2 Hz), 7.90 (d, 1H, J=9 Hz).

(4) Ethyl [[3-[2-[2-(2,4-dichlorophenyl)-5-isopropyl-4-oxazolyl]ethyl]-5-methyl-1,2-benzisoxazol-6-yl]oxyacetate The desired compound was obtained in an analogous manner as in (4) of Example 5.

Yield 97%
  $^1$H-NMR (CDCl$_3$, 400 MHz) δ: 1.11 (d, 6H, J=7 Hz), 1.30 (t, 3H, J=7 Hz), 2.23 (s, 3H), 2.91 (m, 1H), 3.04 (t, 2H, J=7 Hz), 3.31 (t, 2H, J=7 Hz), 4.28 (q, 2H, J=7 Hz), 4.69 (s, 2H), 6.80 (s, 1H), 7.24 (s, 1H), 7.33 (dd, 1H, J=2, 8 Hz), 7.51 (d, 1H, J=2 Hz), 7.91 (d, 1H, J=8 Hz).

(5) [3-[2-[2-(2,4-Dichlorophenyl)-5-isopropyl-4-oxazolyl]ethyl]-5-methyl-1,2-benzisoxazol-6-yl]oxyacetic acid The desired compound was obtained in an analogous manner as in (5) of Example 5.

Yield 88% Pale yellow crystal
  mp (dec) 180–184° C.
  $^1$H-NMR (CDCl$_3$, 400 MHz) δ: 1.11 (d, 6H, J=7 Hz), 2.26 (s, 3H), 2.93 (m, 1H), 3.04 (t, 2H, J=7 Hz), 3.30 (t, 2H, J=7 Hz), 4.76 (s, 2H) 6.84 (s, 1H), 7.23 (s, 1H), 7.33 (dd, 1H, J=2, 8 Hz), 7.64 (d, 1H, J=2 Hz), 7.99 (d, 1H, =8 Hz).
  IR(KBr)cm$^{-1}$:1749, 1718, 1625, 1562, 1521, 1457, 1446, 1429, 1388, 1361, 1317, 1284, 1251, 1162, 1103, 1087, 1041, 898, 863, 831, 817, 775, 732, 674, 667, 611.

Example 10

2-[[3-[2-[4-Isopropyl-2-(4-trifluoromethyl)phenyl-5-thiazolyl]ethyl]-5-methyl-1,2-benzisoxazol-6-yl]oxy]-2-methylpropionic acid 2-piperidin-1-yl ethyl ester hydrochloride 2-[[3-[2-[4-Isopropyl-2-(4-trifluoromethyl)phenyl-5-thiazolyl]ethyl]-5-methyl-1,2-benzisoxazol-6-yl]oxy]-2-methylpropionic acid (247 mg, 0.463 mmol) was dissolved in dichloromethane (10.0 mL). To the solution, oxalyl chloride (0.053 mL, 0.60 mmol) and DMF (1-drop) were added while cooling with ice. The mixture was allowed to room temperature, and stirred for 3 hours under nitrogen atmosphere. The solvent was removed under reduced pressure. The acid chloride compound in the residue was dissolved in dichloromethane (10.0 mL). To the solution, piperidine-2-ethanol (90 mg, 0.70 mmol), triethylamine (71 mg, 0.70 mmol) and 4-dimethylaminopyridine (3 mg) were added. The mixture was stirred for 20 hours at room temperature, and poured into ice-cold water. After ethyl acetate was added to the mixture, the organic layer was washed with saline, and then with water, dried over anhydrous sodium sulfate. After the solvent was removed under reduced pressure, the residue was purified by column chromatography on silica gel with hexane/ethyl acetate (3/1) to give 2-[[3-[2-[4-isopropyl-2-(4-trifluoromethyl)phenyl-5-thiazolyl]-ethyl]-5-methyl-1,2-benzisoxazol-6-yl]oxy]-2-methylpropionic acid 2-piperidin-1-yl ethyl ester (190 mg) as colorless oil. The ester compound was dissolved in diethyl ether (4.0 mL). To the solution, hydrogen chloride-diethyl ether solution was added. Crystals were filtered to give the desired compound (160 mg) as white crystal (yield 51%).
  mp 75–80° C.
  $^1$H-NMR (CDCl$_3$, 400 MHz) δ: (Free) 1.24 (d, 6H, J=7 Hz), 1.3–1.4 (m, 2H), 1.5–1.6 (m, 4H) 1.68 (s, 6H), 2.26 (s, 3H), 2.3–2.4 (m, 4H), 2.55 (t, 2H, J=6 Hz), 3.04 (m, 1H), 3.23 (t, 2H, J=8 Hz), 3.34 (t, 2H, J=8 Hz), 4.31 (t, 2H, J=6 Hz), 6.86 (s, 1H), 7.23 (s, 1H), 7.65 (d, 2H, J=9 Hz), 8.00 (d, 2H, J=9 Hz).

Example 11

Pharmacological Experiment 1

(1) Measurement of PPARα, γ, δ transactivation activity

PPARα, γ, δ transactivation activity of each compound [Examples 1–4] was measured in the manner described below.

I. Method

1) Material

CV-1 cells were obtained from Tohoku University Aging Medical Laboratory, Medical Cell Collection Center. All test compounds were dissolved in dimethylsulfoxide (DMSO). Final concentration of DMSO was 0.1%.

2) Plasmid

Receptor expression plasmid (GAL4-hPPARα, LBD GAL4-hPPARγLBD, GAL4-hPPARδ LBD), Reporter plasmid (UASx4-TK-LUC), and β-galactosidase expression plasmid (βGAL) similar to Kliewer, S. A., et al., ((1992) Nature, 358:771–774) were used.

3) Transfection

CV-1 cells were seeded in 24 well culture plates at $2\times10^5$ cells per well, and cultured for 24 hours OPTI-MEM I Reduced Serum Medium (Life Technologies, 500 μL/well) containing 4%-fetal bovine serum (FBS). After washing with OPTI-MEM, transfection mixture (250 μL/well) containing 0.03 μg of GAL4-hPPARδ LBD, 0.25 μg of UASx4-TK-LUC, 0.35 μg of βGAL, and 2 μL of lipofection reagent, DMRIE-C (Life Technologies) were added. The cells were incubated for 5 hours at 37° C.

4) Cell Treatment by Addition of Test Compound

The cells were washed and incubated for 40 hours in the presence of the test compound (final concentration was $10^{-6}$ M).

5) Measurement of the Level of Reporter Gene Expression

The culture medium was removed and the cells were washed with PBS twice. A solubilizing buffer (100 μL/well) containing 25 mM Tris-PO₄ (pH 7.8), 15% v/v glycerol, 2% CHAPS, 1% Lecithin, 1% BSA, 4 mM EGTA (pH 8.0), 8 mM MgCl$_2$, 1 mM DTT was added. After the incubation for 10 minutes at room temperature, a portion (20 μL) of the solution was transferred into a 96-well plate. Subsequently, 100 μL of luciferase substrate solution (Piccagene: available from Nippon Gene Co., Ltd.) was added, and a luminous intensity per one second (luciferase activety) was measured using a microluminoreader (Type MLR-100, Corona Electrics Co., Ltd.). Each luciferase activety was corrected by the transfection efficiency which was calculated from β-galactosidase activity. The assay method of β-galactosidase activity was as follows: A portion (50 μL) of the solubilized sample was transferred into another 96-well plate; 100 μL of ONPG (2-nitrophenyl-β-galactopyranoside) solution was added and incubated for 5 minutes at room temperature. 50 μL of a reaction stopping solution (1M sodium carbonate solution) was added. Then the absorbance at 414 nm was measured.

A relative PPAR activity was calculated as follows: 0% (luciferase activity of cells treated with DMSO (0.1%) alone), 100% (luciferase activity of cells treated with a control (PPARα: $10^{-4}$ M WY-165041, PPARγ: $10^{-5}$ M Rosiglitazone, PPARδ: $10^{-4}$ M L-165041))

II. Results

The results are shown in Table 25.

TABLE 25

|  | α | γ | δ |
|---|---|---|---|
| Example 1 | 0.1 | 9.4 | 76.9 |
| Example 2 | 8.0 | 3.2 | 67.8 |
| Example 4 | 85.0 | 9.5 | 59.9 |

It is clear from Table 25 that the compounds of Examples have potent PPARδ transactivation activity. Particularly, the compounds of Examples 1 and 2 show selective PPARδ transactivation activity.

Example 52

Pharmacological Tests 2

PPAR transactivation activities of the compounds of Examples 5–10 were assayed in the same manner as described in Example 11. The results are shown in Table 26.

TABLE 26

| Test compound | α | γ | δ |
|---|---|---|---|
| Example 5 | 0 | 0 | 75 |
| Example 6 | 0 | 0 | 54 |
| Example 7 | 0 | 0 | 63 |
| Example 8 | 0 | 0 | 61 |
| Example 9 | 0 | 2 | 86 |
| Example 10 | 3 | 0 | 75 |
| GW-2433 | 64 | 7 | 52 |
| GW-501516 | 0 | 1 | 90 |

Relative activities for PPAR transactivation were shown.

Each value represents as % of control. Cells were cultured in the presence of compounds at $10^{-7}$ M except that PPARδ of Examples 5, 6 and 7 were assayed at $10^{-8}$ M.

Positive Control:
α: $10^{-4}$ M WY-14643
γ: $10^{-5}$ M Rosiglitazone
δ: $10^{-4}$ M L-165041

It is clear from Table 26 that the compounds of Examples 6–10 have potent and selective PPARδ transactivation activities.

Example 13

Pharmacological Experiment 2

HDL Cholesterol Elevating Effect

I. Method

HDL cholesterol elevating effect was measured by using db/db mice, which are hereditary obesity mice. The db/db mice (10 weeks old) were divided into groups based on serum HDL cholesterol levels. Each of the compounds of the present invention (compounds synthesized in Examples 4 and 10) and GW-501516 was orally administered for one week twice daily. Mice of the control group (to which no agent was administered) were orally given 1% methyl cellulose solution. After 16 hours from the final administration, blood sample was collected, and serum HDL cholesterol level was measured. HDL cholesterol was separated by electrophoresis on agarose gels (Chol/Trig Combo, Helena Laboratories). Serum total cholesterol levels were measured enzymaticallly using a kit (Pure Auto, Daiichi Chemicals) by an automatic analyzer (7060E type, Hitachi Ltd.). HDL cholesterol levels were calculated from total cholesterol levels and HDL cholesterol/total cholesterol ratios.

II. Results

Serum HDL cholesterol levels of experiments groups are shown in Table 27. Each value represents as % of the control group.

TABLE 27

| Test compound | Dose (mg/kg/b.i.d.) | Ratio of increasing HDL cholesterol (% to control) |
|---|---|---|
| Example 6 | 10 | 164 |
| GW-501516 | 10 | 149 |

As shown in Table 6, the compound obtained in Example 6 has a potent HDL cholesterol elevating effect.

The invention claimed is:

1. A compound having the following formula (I) or a salt thereof:

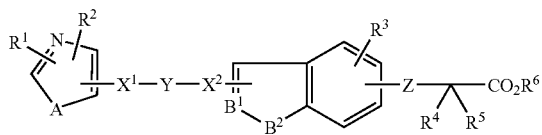

(wherein A is O, S or $NR^7$ in which $R^7$ is hydrogen or $C_{1-8}$ alkyl;

$B^1$ is CW or N in which W is hydrogen or a bond;

$B^2$ is O, S or $NR^8$ in which $R^8$ is hydrogen or $C_{1-8}$ alkyl;

each of $X^1$ and $X^2$ is O, S, NH, NHC(=O), C(=O), C(=N—$OR^9$), CH($OR^{10}$), C=C, C≡C or a bond in which each of $R^9$ and $R^{10}$ is hydrogen or $C_{1-8}$ alkyl;

Y is a $C_{1-8}$ alkylene chain, which can be substituted with $C_{1-8}$ alkyl or $C_{1-8}$ alkyl substituted with 1–3 halogens;

Z is NH, O or S $R^1$ is aryl, which can be substituted with a group or atom selected from the group consisting of $C_{1-8}$ alkyl, $C_{1-8}$ alkoxy, $C_{1-8}$ alkyl substituted with 1–3 halogens, hydroxyl, nitro, amino, phenyl, pyridyl and halogen, or a heterocyclic group having five to eight membered ring comprising one to three hetero atoms selected from the group consisting of nitrogen, oxygen and sulfur and the other atoms consisting of carbon (benzene ring can be condensed with the heterocyclic ring);

$R^2$ is $C_{2-8}$ alkyl, $C_{1-8}$ alkyl substituted with 1–3 halogens, $C_{3-7}$ cycloalkyl, $C_{2-8}$ alkenyl, $C_{2-8}$ alkynyl, alkyl (comprising $C_{1-4}$ alkyl moiety) substituted with aryl, which can be substituted with a group or atom selected from the group consisting of $C_{1-8}$ alkyl, $C_{1-8}$ alkoxy, $C_{1-8}$ alkyl substituted with 1–3 halogens, hydroxyl, nitro, amino, phenyl, pyridyl and halogen, or alkyl (comprising $C_{1-4}$ alkyl moiety) substituted with a heterocyclic group having five to eight membered ring (comprising one to three hetero atoms selected from the group consisting of nitrogen, oxygen and sulfur and the other atoms consisting of carbon);

$R^3$ is halogen, trifluoromethyl, $C_{1-8}$ alkyl, $C_{2-8}$ alkenyl or $C_{2-8}$ alkynyl;

each of $R^4$ and $R^5$ is hydrogen, $C_{1-8}$ alkyl or $C_{1-8}$ alkyl substituted with 1–3 halogens; and $R^6$ is hydrogen, $C_{1-8}$ alkyl substituted with amino, $C_{1-8}$ alkyl or alkali metal;

provided that each of Z and $R^3$ is attached to the benzene ring, and $X^2$ is not attached to the benzene ring.

2. A compound or a salt of thereof defined in claim 1, wherein $R^1$ is attached to the 2nd position of the oxazole, thiazole or imidazole ring.

3. A compound or a salt thereof defined in claim 1, wherein $B^1$ is N, and $B^2$ is O.

4. A compound or a salt thereof defined in claim 1, wherein $R^6$ is hydrogen.

5. A compound or a salt thereof defined in claim 1, wherein $X^2$ is a bond.

6. A compound or a salt thereof defined in claim 1, wherein $X^1$ is a bond.

7. A compound or a salt thereof defined in claim 1, wherein $R^1$ is aryl substituted with a group or atom selected from the group consisting of $C_{1-8}$ alkyl, $C_{1-8}$ alkoxy, $C_{1-8}$ alkyl substituted with 1–3 halogens, hydroxyl, nitro, amino, phenyl, pyridyl and halogen.

8. A compound or a salt thereof defined in claim 1, wherein $R^2$ is $C_{2-8}$ alkyl.

9. A compound or a salt thereof defined in claim 1, wherein $R^3$ is $C_{1-8}$ alkyl or $C_{2-8}$ alkenyl.

10. A pharmaceutical composition which comprises a compound or a salt thereof of claim 1 and a pharmaceutically acceptable carrier or diluent.

* * * * *